US009193777B2

(12) United States Patent
Burnett, Jr. et al.

(10) Patent No.: US 9,193,777 B2
(45) Date of Patent: Nov. 24, 2015

(54) METHOD OF TREATING CARDIAC ARRHYTHMIA WITH LONG ACTING ATRIAL NATRIURETIC PEPTIDE(LA-ANP)

(71) Applicants: Mayo Foundation for Medical Education and Research, Rochester, MN (US); University of Iowa Research Foundation, Iowa City, IA (US)

(72) Inventors: John C. Burnett, Jr., Rochester, MN (US); Timothy M. Olson, Rochester, MN (US); Leonid V. Zingman, Iowa City, IA (US); Denice Marie Hodgson-Zingman, Iowa City, IA (US)

(73) Assignees: Mayo Foundation for Medical Education and Research, Rochester, MN (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 13/889,865

(22) Filed: May 8, 2013

(65) Prior Publication Data
US 2013/0303454 A1 Nov. 14, 2013

Related U.S. Application Data

(63) Continuation of application No. 13/382,962, filed as application No. PCT/US2010/041339 on Jul. 8, 2010, now abandoned.

(60) Provisional application No. 61/224,303, filed on Jul. 9, 2009.

(51) Int. Cl.
*C07K 14/58* (2006.01)
*A61K 38/22* (2006.01)

(52) U.S. Cl.
CPC ............. *C07K 14/58* (2013.01); *A61K 38/2242* (2013.01)

(58) Field of Classification Search
CPC ... A61K 38/00; A61K 2300/00; A61K 35/12; A61K 38/2242; C07K 7/08; C07K 14/58; G01N 2800/326; Y10S 530/858; A61B 5/046
See application file for complete search history.

(56) References Cited

U.S. PATENT DOCUMENTS

| | | | |
|---|---|---|---|
| 4,034,074 A | 7/1977 | Miles | |
| 4,098,876 A | 7/1978 | Piasio et al. | |
| 4,161,521 A | 7/1979 | Veber et al. | |
| 4,233,402 A | 11/1980 | Maggio et al. | |
| 4,683,195 A | 7/1987 | Mullis et al. | |
| 4,728,721 A | 3/1988 | Yamamoto et al. | |
| 4,757,048 A | 7/1988 | Lewicki et al. | |
| 4,935,492 A | 6/1990 | Lewicki et al. | |
| 4,938,763 A | 7/1990 | Dunn et al. | |
| 5,226,325 A | 7/1993 | Komurasaki et al. | |
| 5,278,201 A | 1/1994 | Dunn et al. | |
| 5,278,202 A | 1/1994 | Dunn et al. | |
| 5,296,347 A | 3/1994 | LaMotte | |
| 5,410,016 A | 4/1995 | Hubbell et al. | |
| 5,501,863 A | 3/1996 | Rossling et al. | |
| 5,529,914 A | 6/1996 | Hubbell et al. | |
| 5,580,859 A | 12/1996 | Felgner et al. | |
| 5,589,466 A | 12/1996 | Felgner et al. | |
| 5,691,310 A | 11/1997 | Vesely | |
| 5,698,213 A | 12/1997 | Jamiolkowski et al. | |
| 6,013,630 A | 1/2000 | Shimkets | |
| 6,165,458 A | 12/2000 | Foldvari | |
| 6,312,679 B1 | 11/2001 | Tomalia et al. | |
| 6,407,211 B1 | 6/2002 | Burnett | |
| 6,410,044 B1 | 6/2002 | Chudzik et al. | |
| 6,818,619 B2 | 11/2004 | Burnett, Jr. et al. | |
| 6,833,447 B1 | 12/2004 | Goldman | |
| 7,026,293 B2 | 4/2006 | Kitakaze | |
| 7,276,481 B2 | 10/2007 | Golembo | |
| 7,345,142 B2 | 3/2008 | Cohen | |
| 7,384,917 B2 | 6/2008 | Burnett | |
| 7,754,852 B2 | 7/2010 | Burnett, Jr. et al. | |
| 7,795,221 B2 | 9/2010 | Sharma | |
| 7,803,901 B2 | 9/2010 | Burnett, Jr. et al. | |
| 7,964,564 B2 | 6/2011 | Burnett | |
| 8,063,191 B2 | 11/2011 | Burnett, Jr. et al. | |
| 8,283,318 B2 | 10/2012 | Chen | |
| 8,324,162 B2 | 12/2012 | Simari | |
| 8,357,656 B2 | 1/2013 | Simari | |
| 8,455,438 B2 | 6/2013 | Burnett | |
| 8,530,422 B2 | 9/2013 | Chen | |
| 8,642,550 B2 | 2/2014 | Dickey | |
| 8,741,842 B2 | 6/2014 | Burnett | |
| 8,835,601 B2 | 9/2014 | Chen | |
| 2004/0086976 A1 | 5/2004 | Fleer et al. | |

(Continued)

FOREIGN PATENT DOCUMENTS

| | | |
|---|---|---|
| EP | 0045665 | 9/1985 |
| WO | WO 93/16687 | 9/1993 |
| WO | WO9820165 A3 | 11/1998 |
| WO | WO 99/57318 | 11/1999 |
| WO | WO 2004/047871 | 6/2004 |
| WO | WO 2004/071736 | 8/2004 |
| WO | WO 2006/017852 | 2/2006 |
| WO | WO 2008/061355 | 5/2008 |
| WO | WO 2009/086126 | 9/2009 |
| WO | WO 2012/058585 | 5/2012 |

OTHER PUBLICATIONS

GenBank Accession No. AJ712145 CMPD01 *Homo sapiens* cDNA clone CMPD10397, mRNA sequence-database entry date Jun. 30, 2004, 1 page.

(Continued)

*Primary Examiner* — Elly-Gerald Stoica
(74) *Attorney, Agent, or Firm* — Fish & Richardson P.C.

(57) ABSTRACT

Materials and Methods related to making and using natriuretic polypeptides having a mutation that results in an extended carboxy terminus.

3 Claims, 9 Drawing Sheets

(56) References Cited

U.S. PATENT DOCUMENTS

| | | |
|---|---|---|
| 2007/0042957 A1 | 2/2007 | Burnett |
| 2010/0266704 A1 | 10/2010 | Ahlheim et al. |
| 2011/0152194 A1 | 6/2011 | Burnett, Jr. et al. |
| 2011/0223230 A1 | 9/2011 | Hersel |
| 2012/0010142 A1 | 1/2012 | Burnett |
| 2012/0053123 A1 | 3/2012 | Burnett |
| 2012/0108514 A1 | 5/2012 | Burnett, Jr. et al. |
| 2012/0277155 A1 | 11/2012 | VanAntwerp |
| 2014/0005358 A1 | 1/2014 | Lee |
| 2014/0066367 A1 | 3/2014 | Chen |
| 2014/0274901 A1 | 9/2014 | Ichiki |

OTHER PUBLICATIONS

GenBank Accession No. BC005893, dated Jul. 15, 2006, 3 pages.
PubMed search for atrial natriuretic peptide; Nov. 24, 2009; 5 pages.
PubMed search for brain natriuretic peptide; Nov. 24, 2009; 3 pages.
PubMed search for C-type natriuretic peptide; Nov. 24, 2009; 4 pages.
PubMed search for DNP; Nov. 24, 2009; 4 pages.
Vesely, "Atrial natriuretic peptides in pathophysiological diseases," Cardiovascular research, 51: 647-658, 2001.
Vesely, "Natriuretic peptides and acute renal failure," Am. J. Physiol. Renal.Physiol., 285: F167-F177, 2003.
International Search Report and Written Opinion for PCT/US2006/36227, mailed Nov. 20, 2008, 5 pages.
Deckard and Ebright, "Therapeutic hypothermia after cardiac arrest: What, why, who, and how" American Nurse Today., 6(7):23-28, Jul. 2011.
Funder and Reincke, "Aldosterone: a cardiovascular risk factor?" Biochim Biophys Acta., 1802(12):1188-1192, Epub Aug. 13, 2010.
Gaddam et al., "Aldosterone and cardiovascular disease," Curr Probl Cardiol., 34(2):51-84, Feb. 2009.
International Search Report and Written Opinion in International Application No. PCT/US2010/041339, mailed Mar. 15, 2011, 13 pages.
International Preliminary Report on Patentability in International Application No. PCT/US2010/041339, mailed Jan. 19, 2012, 7 pages.
Almquist et al. "Synthesis and biological activity of a ketomethylene analog of a tripeptide inhibitor of angiotensin converting enzyme," J. Med. Chem., 1980, 23(12):1392-1398.
Banga. "Theme Section: Transdermal Delivery of Proteins," Pharm. Res., 2007, 24(7): 1357-1359.
Braunwald. "Shattuck Lecture: Cardiovascular Medicine at the Turn of the Millennium: Triumphs, Concerns and Opportunities," N. Engl. J. Med., 1997, 337:1360-1369.
Brugada et al. "Identification of a Genetic Locus for Familial Atrial Fibrillation," N. Engl. J. Med., 1997, 336:905-911.
Burnett et al. "Atrial natriuretic peptide elevation in congestive heart failure in the human," Science, 1986, 231:1145-1147.
Cataliotti et al. "Oral Brain Natriuretic Peptide: A Novel Strategy for Chronic Protein Therapy for Cardiovascular Disease," Trends Cardiovasc. Med., 2007, 17:10-14.
Cataliotti et al. "Chronic actions of a novel oral B-type natriuretic peptide conjugate in normal dogs and acute actions in angiontensin II mediated hypertension," Circulation, 2008, 118:1729-1736.
Chaurand et al. "Peptide and Protein Identification by Matrix-Assisted Laser Desorption Ionization (MALDI) and MALDI-Post-Source Decay Time-of-Flight Mass Spectrometry," J. Am. Soc. Mass Spectrom., 1999, 10:91-103.
Chen et al. "KCNQ1 Gain-of-function mutation in familial atrial fibrillation," Science, 2003, 299:251-254.
Cole et al. "The EBV-Hybridoma Technique and its application to human lung cancer," Monoclonal Antibodies and Cancer Therapy, 1985, pp. 77-96.
Cote et al. "Generation of human monoclonal antibodies reactive with cellular antigens," Proc. Natl. Acad. Sci. USA, 1983, 80:2026-2030.
Darbar et al. "Familial atrial fibrillation is a genetically heterogeneous disorder," J. Am. Coll. Cardiol., 2003, 41(12):2185-2192.
Dickey et al. "A familiar mutation renders atrial natriuretic peptide resistant to proteolytic degradation," J. Biol. Chem., 2009, 284: 19196-19202.
Fenelon et al. "Examination of the in vivo cardiac electrophysiological effects of nesiritide (human brain natriuretic peptide) in conscious dogs," J. Cardiac Failure, 2002, 8:320-325.
Fox et al. "Parental atrial fibrillation as a risk factor for atrial fibrillation in offspring," JAMA, 2004, 291:2851-2855.
Gevaert et al. "Protein idlentification based on matrix assisted laser desorption/ionization-post source decaymass spectrometry," Electrophoresis, 2001, 22:1645-1651.
Goebel and Neubert. "Dermal Peptide Delivery Using Colloidal Carrier Systems," Skin Pharmacol. Physiol., 2008, 21:3-9.
Gollob et al. "Somatic Mutations in the Connexin 40 Gene (GJA5) in Atrial Fibrillation," N. Engl. J. Med., 2006, 354:2677-2688.
Guatelli et al. "Isothermal, in vitro amplification of nucleic acids by a multienzyme reaction modeled after retroviral replication," Proc. Natl. Acad. Sci. USA, 1990, 87:1874-1878.
Gudbjartsson et al. "Variants conferring risk of atrial fibrillation on chromosome 4q25 ," Nature, 2007, 448:353-357.
Hann. "On the double bond isostere of the peptide bond: preparation of an enkephalin analogue," J. Chem. Soc. Perkin Trans., 1982, 1:307-314.
Hodgson-Zingman. "Atrial natriuretic peptide frameshift mutation in familial fibrillation," N. Engl. J. Med., 2008, 359(2):158-165.
Holladay et al. "Synthesis of Hydroxyethylene and Ketomethylene Dipeptide Isosteres," Tetrahedron Lett., 1983, 24: 4401-4404.
Hruby. "Conformational Restrictions of Biologically Active Peptides via Amino Acid Side Chain Groups," Life Sci., 1982, 31:189-199.
Hudson et al. "Methionine Enkephalin and Isosteric Analogues," Int. J. Pept. Prot. Res., 1979, 14:177-185.
Hunt et al. "Hypotension and bradycardia during caloric restriction in mice are independent of salt balance and do not require ANP receptor," Am. J. Physiol. Heart Circ. Physiol., 2004, 287(4):H1446-H1451.
Huse et al. "Generation of a Large Combinatorial Library of the Immunoglobulin Repertoire in Phage Lambda," Science, 1989, 246:1275-1281.
Jennings-White et al. "Synthesis of ketomethylene analogs of dipeptides," Tetrahedron Lett., 1982, 23:2533-2534.
Kohler et al. "Continuous cultures of fused cells secreting antibody of predefined specificity," Nature, 1975, 256:495-497.
Komatsu et al. "C-type natriuretic peptide (CNP) in rats and humans," Endocrinol., 1991, 129(2):1104-1106.
Kozbor et al. "The production of monoclonal antibodies from human lymphocytes," Immunology Today, 1983, 4(3):72-79.
Kuhn. "Structure, regulation, and function of mammalian membrane guanylyl cyclase receptors, with a focus on guanylyl cyclase-A," Circ. Res., 2003, 93(8):700-709.
Lebl and Hruby. "Synthesis of cyclic peptides by solid phase methodology," Tetrahedron Lett., 1984, 25(20):2067-2068.
Levin et al. "Natriuretic peptides," N. Engl. J. Med., 1998, 339(5):321-328.
Lewis, "PCR's Competitors Are Alive and Well and Moving Rapidly Towards Commercialization," Genetic Engineering News, 1992, 12:1, 3 pages.
Lloyd-Jones et al. "Lifetime risk for development of atrial fibrillation: The framingham heart study," Circulation, 2004, 110:1042-1046.
Malik et al. "Recent advances in protein and peptide drug delivery systems," Curr. Drug Deliv., 2007, 4(2):141-151.
McKie et al. "A human atrial natriuretic peptide gene mutation reveals a novel peptide with enhanced block pressure-lowering, renal-enhancing, and aldosterone-suppressing actions," J. Am. Coll. Cardiol., 2009, 54(11):1024-1032.
McKie et al. "A novel atrial natriuretic peptide based therapeutic in experimental angiotensin II mediated acute hypertension," Hypertension, 2010, 56:1152-1159.
Miller et al. "Amphiphilic Conjugates of Human Brain Natriuretic Peptide Designed for Oral Delivery: In Vitro Activity Screening," Bioconjugate Chem., 2006, 17: 267-274.

(56) References Cited

OTHER PUBLICATIONS

Morley. "Modulation of the action of regulatory peptides by structural modification," *Trends Pharm. Sci.*, 1980, 463-468.
Myakishev et al. "High-Throughput SNP Genotyping by Allele-Specific PCR with Universal Energy-Transfer-Labeled Primers," *Genome Res.*, 2001, 11:163-169.
Olson et al. "Kv1.5 channelopathy due to KCNA5 loss-of-function mutation causes human atrial fibrillation," *Hum. Mol. Genet.*, 2006, 15:2185-2191.
Olson et al. "Sodium channel mutations and susceptibility to heart failure and atrial fibrillation," *JAMA*, 2005, 293:447-454.
Prausnitz. "A Peptide chaperone for transdermal drug delivery," *Nat. Biotechnol.*, 2006, 24(4):416-417.
Prince et al. "Robust and accurate single nucleotide polymorphism genotyping by dynamic allele-specific hybridization (DASH): design criteria and assay validation," *Genome Res.*, 2001, 11:152-162.
Rossi et al. "Natriuretic peptide levels in atrial fibrillation: a prospective hormonal and Doppler-echocardiographic study," *J. Am. Coll. Cardiol.*, 2000, 35(5):1256-1262.
Schafer and Hawkins, "DNA variation and the future of human genetics," *Nat. Biotechnol.*, 1998, 16:33-39.
Schiller et al. "A novel cyclic opioid peptide analog showing high preference for u-receptors," *Biochem. Biophy. Res. Comm.*, 1985, 127(2):558-564.
Schiller et al. "Synthesis of side-chain to side-chain cyclized peptide analogs on solid supports," *Int. J. Peptide Protein Res.*, 1985, 25:171-177.
Spatola et al. "Structure-activity relationships of enkephalins containing serially replaced thiomethylene amide bond surrogates," *Life Sci.*, 1986, 38:1243-1249.
Spatola, in *Chemistry and Biochemistry of Amino Acid Peptides and Proteins*, "Peptide backbone modifications: A structure-activity analysis of peptides containing amide bond surrogates," B. Weinstein, Ed., Marcel Dekker, New York, 1983, 48 pages.
Steiner et al. "The measurement of cyclic nucleotides by radioimmunoassay," *Adv. Biochem. Psychopharmacol.*, 1970, 3:89-111.
Stoneking et al. Population variation of human mtDNA control region sequences detected by enzymatic amplification and sequence-specific oligonucleotide probes, *Am. J. Hum. Genet.*, 1991, 48:370-382.
Takagi et al. [alpha]-Human Atrial Natriuretic Peptide, Carperitide, Reduces Infarct Size But Not Arrhythmias After Coronary Occlusion/Reperfusion in Dogs. *J Cardiovasc. Pharmacol.*, 2000, 36:22-30.
Takata et al. "The beneficial effect of atrial natriuretic peptide on arrhythmias and myocardial high-energy phosphates after reperfusion," *Cardiovascular Res.*, 1996, 32:286-293.
Tawaragi et al. "Gene and Precursor structures of human c-type natriuretic peptide," *Biochem. Biophys. Res. Commun.*, 1991, 175(2):645-651.
Tsuruda et al. "Brain natriuretic peptide is produced in cardiac fibroblasts and induces matrix metalloproteinases," *Circ. Res.*, 2002, 91:1127-1134.
Underhill et al. "Detection of numerous Y chromosome biallelic polymorphisms by denaturing high-performance liquid chromatography," *Genome Res.*, 1997, 7:996-1005.
Van den Berg et al. "Depletion of atrial natriuretic peptide during longstanding atrial fibrillation," *Europace*, 2004, 6(5):433-437.
Veronese and Mero. "The impact of PEGylation on biological therapies," *Biodrugs*, 2008, 22(5):315-329.
Veronese and Pasut. "PEGylation, successful approach to drug delivery," *Drug Discov. Today*, 2005, 10:1451-1458.
Wang et al., "Albubnp, a recombinant B-type natriuretic peptide and human serum albumin fusion hormone, as a long-term therapy of congestive heart failure," *Pharm. Res.*, 2004, 21:2105-2111.
Weiss. "Hot prospect for new gene amplifier," *Science*, 1991, 254:1292-1293.
Wermeling et al. "Microneedles permit transdermal delivery of a skin-impermeant medication to humans," *Proc. Natl. Acad. Sci. USA*, 2008, 105(6):2058-2063.

Wozakowska-Kaplon. "ANP and B-type peptide: Twins or kins? A different predictive value in atrial fibrillation Natriuretic peptides: Useful biomarkers in predicting the possibility of restoration and maintenance of sinus rhythm in patients with atrial fibrillation undergoing cardioversion," *J Cardiology*, 2010 145 (2):234-235.
Blood Pressure UK, "Diuretics—blood pressure medication," Blood Pressure UK [online], 2008, [retrieved on Nov. 6, 2013]. Retrieved from the Internet: <URL: http://www.bloodpressureuk.org/BloodPressureandyou/Medicines/Medicinetypes/Diuretics>, 4 pages.
Bowie et al, "Deciphering the message in protein sequences: tolerance to amino acid substitutions," Science 247 (4948):1306-1310, 1990.
Ngo et al., "Computational Complexity, Protein Structure Prediction, and the Levinthal Paradox," The Protein Folding Problem and Tertiary Structure Prediction, Merz, Jr. and Grand, Eds, Birkhauser, Boston, pp. 433-506, 1994.
Wang et al, "A single amino acid determines lysophospholipid specificity of the S1P1 (EDG1) and LPA1 (EDG2) phospholipid growth factor receptors," J. Biol Chem., 276(52):49213-49220, Epub Oct. 16, 2001.
Wells, "Additivity of mutational effects in proteins," Biochemistry, 29(37):8509-8517, 1990.
Allen and O'Connor, "Management of acute decompensated heart failure," *Can Med Assoc J*, 176(6):797-805, Mar. 13, 2007.
Arora et al., "Atrial natriuretic peptide is negatively regulated by microRNA-425," *J Clin Invest.*, 123(8):3378-3382, Epub Jul. 15, 2013.
Ausubel et al, Eds. "Mutagenesis of Cloned DNA," *Short Protocols in Molecular Biology*, Green Publishing Associates and John Wiley & Sons, Chpt 8, pp. 8-1 to 8-25, 1992.
Bestle et al., "Cardiovascular, endocrine, and renal effects of urodilatin in normal humans," *Am J Physiol.*, 276(3 Pt 2):R684-R695, Mar. 1999.
Bloch et al., "A serum protease cleaves proANF into a 14-kilodalton peptide and ANF," *Am J Physiol.*, 252(1 Pt 1):E147-E151, Jan. 1987.
Boerrigter et al., "Targeting heme-oxidized soluble guanylate cyclase in experimental heart failure," *Hypertension*, 49(5):1128-1133. Epub Feb. 26, 2007.
Cannone et al., "A genetic variant of the atrial natriuretic peptide gene is associated with cardiometabolic protection in the general community," *J Am Coll Cardiol.*, 58(6):629-636, Aug. 2, 2011.
Cannone et al., "The atrial natriuretic peptide genetic variant rs5068 is associated with a favorable cardiometabolic phenotype in a Mediterranean population," *Diabetes Care.*, 36(9):2850-2856, Epub May 1, 2013.
Carstens et al., "Metabolism and action of urodilatin infusion in healthy volunteers," *Clin Pharmacol Ther.*, 64(1):73-86, Jul. 1998.
Chen et al., "Equimolar doses of atrial and brain natriuretic peptides and urodilatin have differential renal actions in overt experimental heart failure," *Am J Physiol Regul Integr Comp Physiol.*, 288(5):R1093-R1097, Epub Dec. 30, 2004.
Chen et al., "Local renal delivery of a natriuretic peptide a renal-enhancing strategy for B-type natriuretic peptide in overt experimental heart failure," *J Am Coll Cardiol.*, 53(15):1302-1308, Apr. 14, 2009.
Chen et al., "Subcutaneous administration of brain natriuretic peptide in experimental heart failure," *J Am Coll Cardiol.*, 36(5):1706-1712, Nov. 1, 2000.
Chen et al., "Subcutaneous BNP administration in symptomatic human heart failure: a novel therapeutic strategy for congestive heart failure," *J Am Coll Cardiol.*, 35(2s1):240A, Feb. 1, 2000, 1 page.
Costello-Boerrigter et al., "Renal and anti-aldosterone actions of vasopressin-2 receptor antagonism and B-type natriuretic peptide in experimental heart failure," *Circ Heart Fail.*, 3(3):412-419. Epub Feb. 22, 2010.
de Bold et al., "A rapid and potent natriuretic response to intravenous injection of atrial myocardial extract in rats," *Life Sci.*, 28(1):89-94, Jan. 5, 1981.
de Bold, "Atrial natriuretic factor of the rat heart. Studies on isolation and properties," *Proc Soc Exp Biol Med.*, 170(2):133-138, Jun. 1982.
Dietz et al., "Evidence supporting a physiological role for proANP-(1-30) in the regulation of renal excretion," *Am J Physiol Regul Integr Comp Physiol.*, 280(5):R1510-R1517, May 2001.

(56) References Cited

OTHER PUBLICATIONS

Dietz, "Mechanisms of atrial natriuretic peptide secretion from the atrium," *Cardiovasc Res.*, 68(1):8-17, Oct. 1, 2005.

Elsner et al., "Efficacy of prolonged infusion of urodilatin [ANP-(95-126)] in patients with congestive heart failure," *Am Heart J.*, 129(4):766-773, Apr. 1995.

Espiner and Richards, "Atrial natriuretic peptide. An important factor in sodium and blood pressure regulation," *Lancet*, 1(8640):707-710, Apr. 1, 1989.

Fonarow et al., "Factors identified as precipitating hospital admissions for heart failure and clinical outcomes: findings from OPTIMIZE-HF," *Arch Intern Med.*, 168(8):847-854, Apr. 28, 2008.

Forssmann et al., "The renal urodilatin system: clinical implications," *Cardiovasc Res.*, 51(3):450-462, Aug. 15, 2001.

Garbers et al., "Membrane guanylyl cyclase receptors: an update," *Trends Endocrinol Metab.*, 17(6):251-258, Epub Jun. 30, 2006.

Hata et al., "Effects of carperitide on the long-term prognosis of patients with acute decompensated chronic heart failure: the PROTECT multicenter randomized controlled study," *Circ J.*, 72(11):1787-1793, Epub Sep. 24, 2008.

Hawkridge et al., "Quantitative mass spectral evidence for the absence of circulating brain natriuretic peptide (BNP-32) in severe human heart failure," *Proc Natl Acad Sci U S A.*, 102(48):17442-17447, Epub Nov. 17, 2005.

Heublein et al., "Immunoreactivity and guanosine 3',5'-cyclic monophosphate activating actions of various molecular forms of human B-type natriuretic peptide," *Hypertension*, 49(5):1114-1119, Epub Mar. 19, 2007.

Hunter et al., "Measurement of the total proANP product in mammals by processing independent analysis," *J Immunol Methods.*, 370(1-2):104-110, Epub Jun. 15, 2011.

Ibebuogu et al., "Decompensated heart failure is associated with reduced corin levels and decreased cleavage of pro-atrial natriuretic peptide," *Circ Heart Fail.*, 4(2):114-120, Epub Jan. 7, 2011.

Ichiki and Burnett, Jr., "Protein therapeutics for cardiovascular disease: it is all about delivery," *J Am Coll Cardiol.*, 60(24):2558-2560, Epub Nov. 24, 2012.

Ichiki et al., "Abstract 11349: The natriuretic peptide prohormones are processed into active peptides in the normal human circulation and the processing is preserved in heart failure," *Circulation*, 126:A11349, 2012.

Ichiki et al., "All three NP pre/prohormones are processed in human blood into biologically active mature peptides," 16th Annual Scientific Meeting of Heart Failure Society of America, Sep. 10, 2012 [slideshow].

Ichiki et al., "All three NP pre/prohormones are processed in human blood into biologically active mature peptides," *J Card Fail.*, 18(8):S3, Abstract 008, Aug. 2012.

Ichiki et al., "Corin is present in the normal human heart, kidney, and blood, with pro-B-type natriuretic peptide processing in the circulation," *Clin Chem.*, 57(1):40-47, Epub Nov. 12, 2010.

Ichiki et al., "Differential expression of the pro-natriuretic peptide convertases corin and furin in experimental heart failure and atrial fibrosis," *Am J Physiol Regul Integr Comp Physiol.*, 304(2): R102-R109, Jan. 15, 2013.

Ichiki et al., "Pro-Atrial Natriuretic Peptide in vitro and in vivo Normal Canines: A Selective Renal Enhancing Therapeutic," *J Card Fail.*, 19(8):S27, Abstract 074, Aug. 2013; HFSA 2013: Sep. 23, 2013. 17th Annual Scientific Meeting of the Heart Failure Society of America, Orland FL, USA.

Ichiki et al., "Pro-atrial natriuretic peptide in vitro and in vivo normal canines: A selective renal enhancing therapeutic," 17th Annual Scientific Meeting of the Heart Failure Society of America, Orland FL, USA, Sep. 23, 2013, 1 page [abstract].

Ichiki et al., "Pro-atrial natriuretic peptide 1-126 is processed in the human circulation to a mature GC-A activating peptide with therapeutic potential in heart failure," ESC Congress 2013, Amsterdam, Netherland, p. 11, Abstract 66, Aug. 31, 2013.

Ichiki et al., "Pro-atrial natriuretic peptide 1-126 is processed in the human circulation to a mature GC-A activating peptide with therapeutic potential in heart failure," *Eur Heart J.*, 34(suppl 1): doi: 10.1093/eurheartj/eht307.66, Aug. 31, 2013 [abstract].

Ichiki et al., "The natriuretic peptide prohormones are processed into active peptides in the normal human circulation and the processing is preserved in heart failure," American Heart Association Scientific meeting, Nov. 7, 2012, [poster], 1 page.

Ichiki et al., "The processing and degradation of preproANP in the circulation in normal human and patients with heart failure," The 77th Annual Scientific Meeting of Japanese Circulation Society (JCS 2013), Yokohama, Japan, Mar. 16, 2013, 1 page.

Jiang et al., "Ectodomain shedding and autocleavage of the cardiac membrane protease corin," *J Biol Chem.*, 286(12):10066-10072. Epub Feb. 2, 2011.

Kenny and Stephenson, "Role of endopeptidase-24.11 in the inactivation of atrial natriuretic peptide," *FEBS Lett.*, 232(1):1-8, May 9, 1988.

Kenny et al., "Hydrolysis of human and pig brain natriuretic peptides, urodilatin, C-type natriuretic peptide and some C-receptor ligands by endopeptidase-24.11," *Biochem J.*, 29 ( Pt 1):83-88, Apr. 1, 1993.

Lüss et al., "Renal effects of ularitide in patients with decompensated heart failure," *Am Heart J.*, 155(6):1012.e1-8, Jun. 2008.

Mangiafico et al., "Neutral endopeptidase inhibition and the natriuretic peptide system: an evolving strategy in cardiovascular therapeutics," *Eur Heart J.*, 34(12):886-893c, Epub Aug. 31, 2012.

Martin et al., "CD-NP: a novel engineered dual guanylyl cyclase activator with anti-fibrotic actions in the heart," *PLoS One*, 2012;7(12):e52422. Epub Dec. 18, 2012.

Miller et al., "Comparison of novel pro-BNP(1-108) and standard BNP assays in heart failure patients," *Clin Chim Acta.*, 413(9-10):920-926, Epub Feb. 16, 2012.

Mitrovic et al., "Effects of the renal natriuretic peptide urodilatin (ularitide) in patients with decompensated chronic heart failure: a double-blind, placebo-controlled, ascending-dose trial," *Am Heart J.*, 150(6):1239, Dec. 2005.

Mitrovic et al., "Haemodynamic and clinical effects of ularitide in decompensated heart failure," *Eur Heart J.*, 27(23):2823-2832, Epub Oct. 30, 2006.

Morley et al., "K+ channel openers and suppression of airway hyperreactivity," *Trends Pharmacol Sci.*, 15(12):463-468, Dec. 1994.

Mukoyama et al., "Brain natriuretic peptide as a novel cardiac hormone in humans. Evidence for an exquisite dual natriuretic peptide system, atrial natriuretic peptide and brain natriuretic peptide," *J Clin Invest.*, 87(4):1402-1412, Apr. 1991.

Nemer et al., "Gene structure of human cardiac hormone precursor, pronatriodilatin," *Nature*, 312(5995):654-656, Dec. 13-19, 1984.

Newton-Cheh et al., "Association of common variants in NPPA and NPPB with circulating natriuretic peptides and blood pressure," *Nat Genet.*, 41(3):348-353, Epub Feb. 15, 2009.

Niederkofler et al., "Detection of endogenous b-type natriuretic peptide at very low concentrations in patients with heart failure," *Circ Heart Fail.*, 1(4):258-264, Epub Oct. 14, 2008.

Nieminen et al., "Executive summary of the guidelines on the diagnosis and treatment of acute heart failure: the Task Force on Acute Heart Failure of the European Society of Cardiology," *Eur Heart J.*, 26(4):384-416, Epub Jan. 28, 2005.

Nishida et al., "Effects of brain natriuretic peptide on hemodynamics and renal function in dogs," *Jpn J Physiol.*, 40(4):531-540, 1990.

Nomura et al., "Multicenter prospective investigation on efficacy and safety of carperitide as a first-line drug for acute heart failure syndrome with preserved blood pressure: COMPASS: Carperitide Effects Observed Through Monitoring Dyspnea in Acute Decompensated Heart Failure Study," *Circ J.*, 72(11):1777-1786, Epub Oct. 3, 2008.

O'Connor et al., "Effect of nesiritide in patients with acute decompensated heart failure," *N Engl J Med.*, 365(1):32-43, Jul. 7, 2011.

Oikawa et al., "Cloning and sequence analysis of cDNA encoding a precursor for human atrial natriuretic polypeptide," *Nature*, 309(5970):724-726, Jun. 21-27, 1984.

(56) References Cited

OTHER PUBLICATIONS

Potter et al., "Natriuretic peptides, their receptors, and cyclic guanosine monophosphate-dependent signaling functions," *Endocr Rev.*, 27(1):47-72, Epub Nov. 16, 2005.

Potter, "Natriuretic peptide metabolism, clearance and degradation," *FEBS J.*, 278(11):1808-1817, Epub Apr. 7, 2011.

Ralat et al., "Insulin-degrading enzyme modulates the natriuretic peptide-mediated signaling response," *J Biol Chem.*, 286(6):4670-4679. Epub Nov. 22, 2010.

Ronco et al., "Cardio-renal syndromes: report from the consensus conference of the acute dialysis quality initiative," *Eur Heart J.*, 31(6):703-711, print Mar. 2010, Epub Dec. 25, 2009.

Sabrane et al., "Vascular endothelium is critically involved in the hypotensive and hypovolemic actions of atrial natriuretic peptide," *J Clin Invest.*, 115(6):1666-1674, Jun. 2005.

Schulz-Knappe et al., "Isolation and structural analysis of "urodilatin", a new peptide of the cardiodilatin-(anp)-family, extracted from human urine," *Klin Wochenschr.*, 66(17):752-759, Sep. 1988.

Spatola, in *Chemistry and Biochemistry of Amino Acid Peptides and Proteins*, B. Weinstein, ed., Marcel Dekker, New York, p. 267 (1983) [Table of Contents].

Steen and Mann, "The abc's (and xyz's) of peptide sequencing," *Nat Rev Mol Cell Biol.*, 5:699-711, Sep. 2004.

Suwa et al., "Multicenter prospective investigation on efficacy and safety of carperitide for acute heart failure in the 'real world' of therapy," *Circ J.*, 69(3):283-290, Mar. 2005.

van den Akker, "Structural insights into the ligand binding domains of membrane bound guanylyl cyclases and natriuretic peptide receptors," *J Mol Biol.*, 311(5):923-937, Aug. 31, 2001.

Yan et al., "Corin, a mosaic transmembrane serine protease encoded by a novel cDNA from human heart," *J Biol Chem.*, 274(21):14926-14935, May 21, 1999.

Yan et al., "Corin, a transmembrane cardiac serine protease, acts as a pro-atrial natriuretic peptide-converting enzyme," *Proc Natl Acad Sci U S A.*, 97(15):8525-8529, Jul. 18, 2000.

De Palo et al., "Circulating immunoreactive proANP(1-30) and proANP(31-67) in sedentary subjects and athletes," *Clin. Chem.*, 46(6 Pt 1):843-847, Jun. 2000.

US 6,884,780, 04/2005, Drummond (withdrawn)

ANP (SEQ ID NO:5)

```
H. sapiens ANP       SLRRSSCFGGRMDRIGAQSGLGCNSFRY               (SEQ ID NO:5)
Mutant ANP           SLRRSSCFGGRMDRIGAQSGLGCNSFRYRITAREDKQGWA   (SEQ ID NO:6)
P. troglodytes ANP   ···························               (SEQ ID NO:5)
S. scrofa ANP        ···························               (SEQ ID NO:5)
C. familiaris ANP    ···························               (SEQ ID NO:5)
B. taurus ANP        ···························               (SEQ ID NO:5)
O. cuniculus ANP     ························I··               (SEQ ID NO:7)
R. norvegicus ANP    ························I··               (SEQ ID NO:7)
M. musculus ANP      ························I··               (SEQ ID NO:7)
D. rerio ANP         ·KSL·G····L····SS·T····KKG                 (SEQ ID NO:8)
H. sapiens BNP       SPKMVQG·G····RK····SSS····KVL·RH           (SEQ ID NO:9)
H. sapiens CNP       GLSKG····LKL····SM····                     (SEQ ID NO:10)
D. angusticeps DN    EVKYDP····NHV·N····P·L·DPRPNAPSTSA         (SEQ ID NO:11)
```

METHOD OF TREATING CARDIAC ARRHYTHMIA WITH LONG ACTING ATRIAL NATRIURETIC PEPTIDE(LA-ANP)

CROSS-REFERENCE TO RELATED APPLICATIONS

This application is a continuation of U.S. application Ser. No. 13/382,962, filed Jan. 9, 2012, which is a National Stage application under 35 U.S.C. 371 of International Application No. PCT/US2010/041339, having an International Filing Date of Jul. 8, 2010, which claims benefit of priority from U.S. Provisional Application Ser. No. 61/224,303, filed on Jul. 9, 2009.

STATEMENT AS TO FEDERALLY SPONSORED RESEARCH

This invention was made with government support under grant nos. HL075495, HL76611, and HL36634, awarded by the National Institutes of Health. The government has certain rights in the invention.

TECHNICAL FIELD

This document relates to a variant natriuretic peptide, and to methods for using the variant peptide to diagnose or determine predisposition to atrial fibrillation.

BACKGROUND

Natriuretic polypeptides are polypeptides that can cause natriuresis—increased sodium excretion in the urine. Such polypeptides can be produced by brain, heart, kidney, and/or vascular tissue. The natriuretic polypeptide family in humans includes the cardiac hormones atrial natriuretic peptide (ANP), B-type natriuretic peptide (BNP), C-type natriuretic peptide (CNP), and urodilatin (URO). Natriuretic polypeptides function via well-characterized guanylyl cyclase receptors (i.e., NPR-A for ANP, BNP, and URO; and NPR-B for CNP) and the second messenger cyclic 3'5' guanosine monophosphate (cGMP) (Kuhn (2003) *Circ. Res.* 93:700-709; Tawaragi et al. (1991) *Biochem. Biophys. Res. Commun.* 175: 645-651; and Komatsu et al. (1991) *Endocrinol.* 129:1104-1106).

Cardiac arrhythmia includes a heterogeneous group of conditions in which there is abnormal electrical activity in the heart. The heart may beat too quickly or too slowly, and may be regular or irregular. Atrial fibrillation is a common arrhythmia that is familial in a small subset of cases. Atrial fibrillation is the most common sustained cardiac arrhythmia, constituting a growing epidemic in the aging population with a 25% lifetime risk (Braunwald (1997) *N. Engl. J. Med.* 337:1360-1369; and Lloyd-Jones et al. (2004) *Circulation* 110:1042-1046). It develops as a paroxysmal disorder characterized by rapid, irregular electrical activation of the atria and can be associated with palpitations, syncope, thromboembolic stroke, and congestive heart failure. Valvular, ischemic, hypertensive, and myopathic heart disease are the most common causes of acquired atrial fibrillation. A genetic basis for atrial fibrillation also is evident in population-based studies (Fox et al. (2004) *JAMA* 291:2851-2855; and Gudbjartsson et al. (2007) *Nature* 448:353-357) and in a subset of patients with familial disease (Brugada et al. (1997) *N. Engl. J. Med.* 336:905-911; and Darbar et al. (2003) *J. Am. Coll. Cardiol.* 41:2185-2192). Human genetic investigations have identified atrial fibrillation-associated mutations in cardiac ion channels (Chen et al. (2003) *Science* 299:251-254; Olson et al. (2005) *JAMA* 293:447-454; and Olson et al. (2006) *Hum. Mol. Genet.* 15: 2185-2191) and gap junction proteins (Gollob et al. (2006) *N. Engl. J. Med.* 354:2677-2688), implicating myocellular derangements in ion flux. The molecular basis of atrial fibrillation remains unknown, however, in the majority of cases.

SUMMARY

This document is based on part on the identification of a novel mutation in the atrial natriuretic peptide (ANP) gene that segregates with familial atrial fibrillation, thus indicating an unexpected association between a circulating hormone defect and susceptibility to arrhythmia. An atrial fibrillation locus to chromosome 1p36-p35 in a family with 11 clinically affected members, and a heterozygous frameshift mutation in the gene encoding atrial natriuretic peptide was mapped and identified. Circulating chimeric atrial natriuretic peptide was detected in high concentration in individuals with the mutation, and shortened atrial action potentials were demonstrated in an isolated heart model, creating a possible substrate for atrial fibrillation. This document implicates perturbation of the atrial natriuretic peptide-cyclic GMP pathway in cardiac electrical instability.

In one aspect, this document features a method for treating a cardiac arrhythmia in a mammal in need thereof, comprising administering to the mammal a polypeptide comprising the amino acid sequence set forth in SEQ ID NO:13, or the amino acid sequence set forth in SEQ ID NO:13 having less than five amino acid additions, subtractions, and substitutions. The polypeptide can comprise an amino acid sequence present in an ANP polypeptide, an amino acid sequence present in a BNP polypeptide, an amino acid sequence present in an CNP polypeptide, or an amino acid sequence present in an DNP polypeptide. The polypeptide can comprise the amino acid sequence set forth in SEQ ID NO:13. The polypeptide can comprise the amino acid sequence set forth in SEQ ID NO:13 having less than five amino acid additions, subtractions, and substitutions, or the amino acid sequence set forth in SEQ ID NO:13 having less than four amino acid additions, subtractions, and substitutions.

In another aspect, this document features a method for treating a cardiac arrhythmia in a mammal in need thereof, comprising administering to the mammal a nucleic acid encoding a polypeptide that comprises the amino acid sequence set forth in SEQ ID NO:13, or the amino acid sequence set forth in SEQ ID NO:13 having less than five amino acid additions, subtractions, and substitutions.

In another aspect, this document features a method for diagnosing a cardiac arrhythmia in a mammal, comprising providing a biological sample from the mammal and assessing the biological sample to determine whether the biological sample comprises a polypeptide comprising the amino acid sequence set forth in SEQ ID NO:13 and, if the biological sample comprises the polypeptide, diagnosing the mammal as having a cardiac arrhythmia.

This document also features a method for determining whether a mammal is predisposed to develop a cardiac arrhythmia in a mammal, comprising providing a biological sample from the mammal and assessing the biological sample to determine whether the biological sample comprises (a) a polypeptide comprising the amino acid sequence set forth in SEQ ID NO:13 or (b) a nucleic acid encoding the polypeptide, and, if the biological sample comprises the polypeptide or nucleic acid, classifying the mammal as being predisposed to develop a cardiac arrhythmia or, if the biological sample does not comprise the polypeptide or nucleic acid, classifying the mammal as not being predisposed to develop a cardiac arrhythmia.

In addition, this document features the use of a polypeptide in the manufacture of a medicament for treating a cardiac arrhythmia, wherein the polypeptide comprises the amino acid sequence set forth in SEQ ID NO:13, or the amino acid sequence set forth in SEQ ID NO:13 having less than five amino acid additions, subtractions, and substitutions. The polypeptide can comprise an amino acid sequence present in an ANP polypeptide, an amino acid sequence present in a BNP polypeptide, an amino acid sequence present in an CNP polypeptide, or an amino acid sequence present in an DNP polypeptide. The polypeptide can comprise the amino acid sequence set forth in SEQ ID NO:13. The polypeptide can comprise the amino acid sequence set forth in SEQ ID NO:13 having less than five amino acid additions, subtractions, and substitutions, or the amino acid sequence set forth in SEQ ID NO:13 having less than four amino acid additions, subtractions, and substitutions.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A) and LA-ANP (SEQ ID NO:6; FIG. 1B).

In FIG. 4A, a representative monophasic action potential (MAP) is shown at baseline and following a 40-minute perfusion with wild-type ANP. MAP duration at 90% repolarization ($MAPD_{90}$) was not significantly changed by ANP. In FIG. 4B, a representative MAP following a 40-minute perfusion with the mutant form of ANP (mANP) demonstrated shortening of $MAPD_{90}$ from 47 to 41 msec. In FIG. 4C, mANP (n=8) and wild-type ANP (n=10) perfusion for 40 minutes demonstrated a significant decrease in $MAPD_{90}$ for mANP versus baseline (9±2 msec, *$p<0.01$), but not for wild-type ANP versus baseline (0.7±1.7 msec, n=NS). $MAPD_{90}$ also was significantly different following mANP versus wild-type ANP perfusion ($p<0.01$). In FIG. 4D, mANP (n=7) and wild-type ANP (n=6) perfusion for 40 minutes resulted in a trend toward reduction in effective refractory period (ERP) versus baseline for mANP (7.1±2.4 msec, $p=0.08$) but not wild-type ANP (n=NS), and a significant change in ERP for mANP versus wild-type ANP ($p<0.05$).

FIG. 5A is a diagram depicting how the NPPA mutation generates a chimeric ANP protein. As indicated in FIG. 5A, a common 454 C>T polymorphism (circled nucleotides in SEQ ID NOS:1 and 2) in exon 3 of wild-type NPPA (individual 111.4) results in ANP with or without a carboxy-terminal pair of arginine residues, which are removed in post-translational processing. The mutant allele (individual 111.2), on the background of the 454C variant, harbors a 2-bp frameshift deletion (456-457delAA; cDNA clone BC005893; boxed in FIG. 5A), disrupting the stop codon and generating a 40-amino acid chimeric protein with an anomalous 12-residue carboxyl-terminal tail. SEQ ID NO:3 is the amino acid sequence of the normal C-terminal tyrosine plus the 12-residue tail; SEQ ID NO:4 is a nucleotide sequence encoding SEQ ID NO:3. FIG. 5B shows an alignment of mature human ANP SEQ ID NO:5) with ANP orthologs (SEQ ID NOS:6-8), demonstrating significant sequence conservation among eukaryotic species. The human paralogs BNP (SEQ ID NO:9) and CNP (SEQ ID NO:10) are divergent, yet retain the "CFGXXXDRIXXXSXLGC" motif (SEQ ID NO:14) common to natriuretic peptides (Potter et al. (2006) *Endocr. Rev.* 27:47-72). Conserved amino acids are shaded. Atrial fibrillation-associated mutant ANP has an extended amino acid carboxyl-terminus (bold) reminiscent of DNP (SEQ ID NO:11), a natriuretic peptide with distinct biological properties found in the green mamba snake.

DETAILED DESCRIPTION

Natriuretic Polypeptides

Figure 1A:
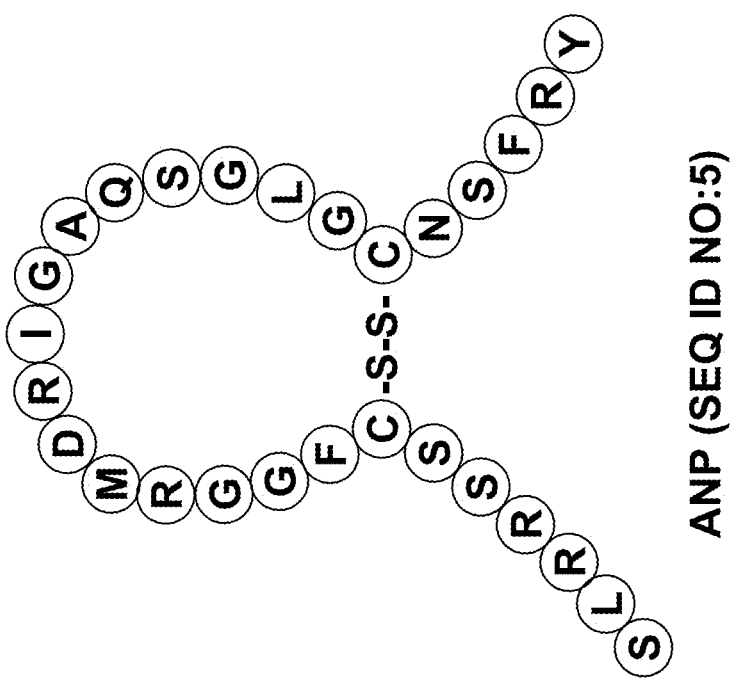
FIGS. 1A and 1B are graphical representations of ANP (SEQ ID NO:5.

This document provides methods and materials related to natriuretic polypeptides. For example, this document provides substantially pure polypeptides having a natriuretic polypeptide activity, nucleic acid molecules encoding polypeptides having a natriuretic polypeptide activity, and host cells containing isolated nucleic acid molecules that encode polypeptides having a natriuretic polypeptide activity. In addition, this document provides methods and materials for inducing a natriuretic or diuretic activity within a mammal. Natriuretic polypeptides can, for example, increase plasma cGMP levels, urinary cGMP excretion, net renal cGMP generation, urine flow, urinary sodium excretion, urinary potassium excretion, hematocrit, plasma BNP immunoreactivity, renal blood flow, and/or plasma ANP immunoreactivity, and decrease renal vascular resistance, proximal and distal fractional reabsorption of sodium, mean arterial pressure, pulmonary capillary wedge pressure, right atrial pressure, pulmonary arterial pressure, plasma renin activity, plasma angiotensin II levels, plasma aldosterone levels, renal perfusion pressure, and/or systemic vascular resistance.

As used herein, the term "natriuretic polypeptide" includes native (naturally occurring, wild type) natriuretic polypeptides (e.g., human ANP, BNP, CNP, and URO, as well as Dendroaspis natriuretic peptide (DNP)), one or more portions of a native natriuretic polypeptide, variants of a native natriuretic polypeptide, or chimeras of native natriuretic polypeptides, portions of native natriuretic polypeptides, or variants of native natriuretic polypeptides or portions of native natriuretic polypeptides. In some embodiments, a natriuretic polypeptide includes only portions of the mature form of a native natriuretic polypeptide. Natriuretic polypeptides containing amino acid sequences from two or more of human CNP, BNP, ANP, URO, and/or Dendroaspis DNP also can be useful.

An "isolated" polypeptide is a polypeptide that (1) is not associated with proteins found in nature, (2) is free of other proteins from the same source (e.g., free of human proteins), (3) is expressed by a cell from a different species, or (4) does not occur in nature. An isolated polypeptide can be, for example, encoded by DNA or RNA, including synthetic DNA or RNA, or some combination thereof.

Amino acid sequences for endogenous human mature natriuretic polypeptides include the following:

ANP: SLRRSSCFGGRMDRIGAQSGLGCNSFRY (SEQ ID NO:5)

BNP: SPKMVQGSGCFGRKMDRISSSSGLGCKVLRRH (SEQ ID NO:9)

CNP: GLSKGCFGLKLDRIGSMSGLGC (SEQ ID NO:10)

URO: TAPRSLRRSSCFGGRMDRIGAQSGLGCNSFRY (SEQ ID NO:12)

In addition, the native Dendroaspis amino acid sequence for DNP is EVKYDPCFGHKIDRINHVSNLGCPSLRDPRPNAPSTSA (SEQ ID NO:11).

Each of these native mature natriuretic polypeptides includes a 17-amino acid ring structure with a cysteine bond between the cysteine residues at positions 1 and 17 (underlined in the above sequences) of the ring.

Chimeric natriuretic polypeptides, which can include amino acid sequences from two or more individual natriuretic polypeptides. In some embodiments, for example, a chimeric polypeptide can include amino acid sequences from ANP and CNP; BNP and CNP; ANP, BNP, and CNP; CNP and URO; CNP and DNP; or CNP, URO, and BNP. Chimeric natriuretic polypeptides typically include a ring structure and cysteine bond from one natriuretic polypeptide (e.g., the ring structure and cysteine bond of ANP, BNP, CNP, DNP, or URO) in combination with one or more amino acid segments from another natriuretic polypeptide. In some embodiments, a chimeric natriuretic polypeptide can include a variant (e.g., a substitution, addition, or deletion) at one or more positions (e.g., one, two, three, four, five, six, seven, eight, nine, or ten positions) with respect to any of SEQ ID NOS:5 to 12, in addition to containing a carboxy terminal extension (e.g., a carboxy terminal extension comprising the amino acid sequence set forth in SEQ ID NO:13).

Natriuretic polypeptides having one or more amino acid substitutions relative to a native natriuretic polypeptide amino acid sequence (also referred to herein as "variant" natriuretic polypeptides) can be prepared and modified as described herein. Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenyalanine, glycine for proline, threonine for serine, serine for threonine, tyrosine for tryptophan, phenylalanine for tyrosine, and/or leucine for valine.

Non-limiting examples of variant chimeric natriuretic polypeptides include a polypeptide can contain the amino acid sequence set forth in SEQ ID NO:13 with one, two, three, four, or five single amino acid residue additions, subtractions, or substitutions. An example of such a polypeptide includes, without limitation, a polypeptide having the amino acid sequence set forth in SEQ ID NO:13 where the threonine is deleted, the tryptophan is replaced with a tyrosine, and a serine is added between the lysine and the glutamine. Another example can be a polypeptide containing a contiguous amino acid sequence that is identical to the first nine amino acid residues set forth in SEQ ID NO:13 and lacking last three residues (i.e., glycine, tryptophan, and alanine)

Any amino acid residue set forth in SEQ ID NO:13 can be subtracted, and any amino acid residue (e.g., any of the 20 conventional amino acid residues or any other type of amino acid such as ornithine or citrulline) can be added to the sequence set forth in SEQ ID NO:13. In some cases, a polypeptide provided herein can contain chemical structures such as ε-aminohexanoic acid; hydroxylated amino acids such as 3-hydroxyproline, 4-hydroxyproline, (5R)-5-hydroxy-L-lysine, allo-hydroxylysine, and 5-hydroxy-L-norvaline; or glycosylated amino acids such as amino acids containing monosaccharides (e.g., D-glucose, D-galactose, D-mannose, D-glucosamine, and D-galactosamine) or combinations of monosaccharides.

Further examples of conservative substitutions that can be made at any position within the polypeptides provided herein are set forth in Table 1.

TABLE 1

Examples of conservative amino acid substitutions

| Original Residue | Exemplary substitutions | Preferred substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleucine | Leu |

In some embodiments, a natriuretic polypeptide can include one or more non-conservative substitutions. Non-conservative substitutions typically entail exchanging a member of one of the classes described above for a member of another class. Such production can be desirable to provide large quantities or alternative embodiments of such compounds. Whether an amino acid change results in a functional polypeptide can readily be determined by assaying the specific activity of the peptide variant using, for example, methods disclosed herein.

A polypeptide provided herein can have a length of, for example, between 17 and 45 amino acid residues (e.g., between 18 and 40, between 22 and 44, between 25 and 45, between 26 and 44, between 27 and 43, between 28 and 42, between 29 and 41, between 30 and 40, between 31 and 39, between 23 and 35, between 25 and 30, or between 30 and 35 amino acid residues). It will be appreciated that a polypeptide with a length of 17 or 45 amino acid residues is a polypeptide with a length between 17 and 45 amino acid residues.

Variant natriuretic polypeptides having conservative and/or non-conservative substitutions (e.g., with respect to any of SEQ ID NOS:3 and 5 to 13), as well as fragments of any of SEQ ID NOS: 3 and 5 to 13, fragments of variants of any of SEQ ID NOS: 3 and 5 to 13, and polypeptides comprising any of SEQ ID NOS: 3 and 5 to 13, variants or fragments of any of SEQ ID NOS: 3 and 5 to 13, or fragments of variants of any of SEQ ID NOS: 3 and 5 to 13, can be screened for biological activity using any of a number of assays, including those described herein. For example, the activity of a natriuretic polypeptide as described herein can be evaluated in vitro by testing its effect on cGMP production in cultured cells (e.g., cultured cardiac fibroblasts, aortic endothelial cells, or glomerular cells). Cells can be exposed to a natriuretic polypeptide (e.g., $10^{-9}$ to $10^{-4}$ M natriuretic polypeptide), and samples can be assayed to evaluate the natriuretic polypeptide effects on cGMP generation. cGMP generation can be detected and measured using, for example, a competitive RIA cGMP kit (Perkin-Elmer, Boston, Mass.).

The activity of a natriuretic polypeptide also can be evaluated in vivo by, for example, testing its effects on factors such as pulmonary capillary wedge pressure, right atrial pressure, mean arterial pressure, urinary sodium excretion, urine flow, proximal and distal fractional sodium reabsorption, plasma renin activity, plasma cGMP levels, urinary cGMP excretion, net renal generation of cGMP, glomerular filtration rate, and left ventricular mass in animals. In some cases, such parameters can be evaluated after induced MI (e.g., MI induced by coronary artery ligation).

The natriuretic polypeptides provided herein typically are cyclic due to disulfide bonds between cysteine residues. In some embodiments, a sulfhydryl group on a cysteine residue can be replaced with an alternative group (e.g., —$CH_2CH_2$—). To replace a sulfhydryl group with a —$CH_2$— group, for example, a cysteine residue can be replaced by alpha-aminobutyric acid. Such cyclic analog polypeptides can be generated, for example, in accordance with the methodology of Lebl and Hruby ((1984) *Tetrahedron Lett.* 25:2067), or by employing the procedure disclosed in U.S. Pat. No. 4,161,521.

In addition, ester or amide bridges can be formed by reacting the OH of serine or threonine with the carboxyl group of aspartic acid or glutamic acid to yield a bridge having the structure —$CH_2CO_2CH_2$—. Similarly, an amide can be obtained by reacting the side chain of lysine with aspartic acid or glutamic acid to yield a bridge having the structure —$CH_2C(O)NH(CH)_4$—. Methods for synthesis of these bridges are known in the art (see, e.g., Schiller et al. (1985) *Biochem. Biophy. Res. Comm.* 127:558, and Schiller et al. (1985) *Int. J. Peptide Protein Res.* 25:171). Other bridge-forming amino acid residues and reactions are provided in, for example, U.S. Pat. No. 4,935,492. Preparation of peptide analogs that include non-peptidyl bonds to link amino acid residues also are known in the art. See, e.g., Spatola et al. (1986) *Life Sci.* 38:1243; Spatola (1983) *Vega Data* 1(3); Morley (1980) *Trends Pharm. Sci.* 463-468; Hudson et al. (1979) *Int. J. Pept. Prot. Res.* 14:177; Spatola, in *Chemistry and Biochemistry of Amino Acid Peptides and Proteins*, B. Weinstein, ed., Marcel Dekker, New York, p. 267 (1983); Hann (1982) *J. Chem. Soc. Perkin Trans.* 1:307; Almquist et al. (1980) *J. Med. Chem.* 23:1392; Jennings-White et al. (1982) *Tetrahedron Lett.* 23:2533; European Patent Application EP 45665; Holladay et al. (1983) *Tetrahedron Lett.* 24:4401; and Hruby (1982) *Life Sci.* 31:189.

In some embodiments, a natriuretic polypeptide can comprise an amino acid sequence as set forth in SEQ ID NOS:3, 5, 6, 7, 8, 9, 10, 11, or 12, but with a particular number of amino acid substitutions. For example, a natriuretic polypeptide can have the amino acid sequence of any one of SEQ ID NOS: 3, 5, 6, 7, 8, 9, 10, 11, or 12, but with one, two, three, four, or five amino acid substitutions. Examples of such amino acid sequences include, without limitation, those set forth in SEQ ID NOS:15-24.

```
                                            (SEQ ID NO: 15)
TLRRSSCFGGRMDRIGAQSGLGCNSFRYRITAREDKQGWA (SEQ ID NO: 16)
SIRRSSCFGGRMDRIGAQSGLGCNSFRYRITAREDKQGWA (SEQ ID NO: 17)
SLKRSSCFGGRMDRIGAQSGLGCNSFRYRITAREDKQGWA
```

SLRKSSCFGGRMDRIGAQSGLGCNSFRYRITAREDKQGWA (SEQ ID NO: 18)

SLRRTSCFGGRMDRIGAQSGLGCNSFRYRITAREDKQGWA (SEQ ID NO: 19)

SLRRSSCFGGRMDRIGAQSGLGCNSFRYRITAREDRQGWA (SEQ ID NO: 20)

SLRRSSCFGGRMDRIGAQSGLGCNSFRYRITAREDKNGWA (SEQ ID NO: 21)

SLRRSSCFGGRMDRIGAQSGLGCNSFRYRITAREDKQPWA (SEQ ID NO: 22)

SLRRSSCFGGRMDRIGAQSGLGCNSFRYRITAREDKQGYA (SEQ ID NO: 23)

SLRRSSCFGGRMDRIGAQSGLGCNSFRYRITAREDKQGWV (SEQ ID NO: 24)

In some embodiments, a natriuretic polypeptide as provided herein can include an amino acid sequence with at least 85% (e.g., 85%, 86%, 87%, 88%, 89%, 90%, 91%, 92%, 93%, 94%, 95%, 96%, 97%, 97.5%, 98%, 98.5%, 99.0%, 99.5%, 99.6%, 99.7%, 99.8%, 99.9%, or 100%) sequence identity to a region of a reference natriuretic polypeptide sequence (e.g., any one of SEQ ID NOS: 3, 5, 6, 7, 8, 9, 10, 11, 12, or 13). Percent sequence identity is calculated by determining the number of matched positions in aligned amino acid sequences, dividing the number of matched positions by the total number of aligned amino acids, and multiplying by 100. A matched position refers to a position in which identical amino acids occur at the same position in aligned amino acid sequences. Percent sequence identity also can be determined for any nucleic acid sequence.

Percent sequence identity is determined by comparing a target nucleic acid or amino acid sequence to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S. government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq c:\seq1.txt-j c:\seq2.txt-p blastn-o c:\output.txt-q-1-r2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a target sequence that is 30 amino acids in length is compared to the sequence set forth in SEQ ID NO:6, (2) the Bl2seq program presents 27 amino acids from the target sequence aligned with a region of the sequence set forth in SEQ ID NO:6 where the first and last amino acids of that 27 amino acid region are matches, and (3) the number of matches over those 27 aligned amino acids is 25, then the 30 amino acid target sequence contains a length of 27 and a percent identity over that length of 92.6 (i.e., 25) 27×100=92.6).

It will be appreciated that different regions within a single amino acid or nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated polypeptides can be produced using any suitable methods, including solid phase synthesis, and can be generated using manual techniques or automated techniques (e.g., using an Applied BioSystems (Foster City, Calif.) Peptide Synthesizer or a Biosearch Inc. (San Rafael, Calif.) automatic peptide synthesizer. Disulfide bonds between cysteine residues can be introduced by mild oxidation of the linear polypeptides using KCN as taught, e.g., in U.S. Pat. No. 4,757,048. Natriuretic polypeptides also can be produced recombinantly, as described herein.

In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

Salts of carboxyl groups of polypeptides can be prepared by contacting the peptide with one or more equivalents of a desired base such as, for example, a metallic hydroxide base (e.g., sodium hydroxide), a metal carbonate or bicarbonate base (e.g., sodium carbonate or sodium bicarbonate), or an amine base (e.g., triethylamine, triethanolamine, and the like). Acid addition salts of polypeptides can be prepared by contacting the polypeptide with one or more equivalents of an inorganic or organic acid (e.g., hydrochloric acid).

Esters of carboxyl groups of polypeptides can be prepared using any suitable means (e.g., those known in the art) for converting a carboxylic acid or precursor to an ester. For example, one method for preparing esters of the present polypeptides, when using the Merrifield synthesis technique, is to cleave the completed polypeptide from the resin in the presence of the desired alcohol under either basic or acidic conditions, depending upon the resin. The C-terminal end of the polypeptide then can be directly esterified when freed from the resin, without isolation of the free acid.

Amides of polypeptides can be prepared using techniques (e.g., those known in the art) for converting a carboxylic acid group or precursor to an amide. One method for amide formation at the C-terminal carboxyl group includes cleaving the polypeptide from a solid support with an appropriate amine, or cleaving in the presence of an alcohol, yielding an ester, followed by aminolysis with the desired amine.

N-acyl derivatives of an amino group of a polypeptide can be prepared by utilizing an N-acyl protected amino acid for the final condensation, or by acylating a protected or unprotected peptide. O-acyl derivatives can be prepared for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

In some embodiments, the natriuretic polypeptides provided herein can have half-lives that are increased relative to the half-life of native natriuretic polypeptides. For example, while the half-life of ANP in humans is about two to five minutes and its metabolic clearance rate is about 14 to 25 ml/min/kg, the elimination half-life of a variant natriuretic polypeptide (e.g., containing SEQ ID NO:13) can be increased by comparison. In some cases, a natriuretic polypeptide provided herein can have a half life that is increased by at least 2-fold (e.g., at least 2-fold, at least 3-fold, at least 4-fold, at least 5-fold, at least 6-fold, at least 7-fold, at least 8-fold, at least 9-fold, or at least 10-fold) as compared to a native natriuretic polypeptide such as ANP, for example. In some embodiments, a natriuretic polypeptide can have an elimination half-life of at least about 5 minutes (e.g., at least about 5 minutes, at least about 7 minutes, at least about 10 minutes, at least about 12 minutes, at least about 15 minutes, at least about 17 minutes, at least about 18 minutes, or at least about 20 minutes).

In some embodiments, a natriuretic polypeptide can be modified by linkage to a polymer such as polyethylene glycol (PEG), or by fusion to another polypeptide such as albumin, for example. In some embodiments, one or more PEG moieties can be conjugated to a natriuretic polypeptide via lysine residues. Linkage to PEG or another suitable polymer, or fusion to albumin or another suitable polypeptide can result in a modified natriuretic polypeptide having an increased half life as compared to an unmodified natriuretic polypeptide. Without being bound by a particular mechanism, an increased serum half life can result from reduced proteolytic degradation, immune recognition, or cell scavenging of the modified natriuretic polypeptide. Methods for modifying a polypeptide by linkage to PEG (also referred to as "PEGylation") or other polymers are known in the art, and include those set forth in U.S. Pat. No. 6,884,780; Cataliotti et al. ((2007) *Trends Cardiovasc. Med.* 17:10-14; Veronese and Mero (2008) *BioDrugs* 22:315-329; Miller et al. (2006) *Bioconjugate Chem.* 17:267-274; and Veronese and Pasut (2005) *Drug Discov. Today* 10:1451-1458, all of which are incorporated herein by reference in their entirety. Methods for modifying a polypeptide by fusion to albumin also are known in the art, and include those set forth in U.S. Patent Publication No. 20040086976, and Wang et al. (2004) *Pharm. Res.* 21:2105-2111, both of which are incorporated herein by reference in their entirety.

A natriuretic polypeptide as provided herein can function through one or more of the guanylyl cyclase receptors through which the native natriuretic polypeptides function. For example, a natriuretic polypeptide as provided herein can bind to and function through the NPR-A receptor through which ANP and BNP function, or through the NPR-B receptor through which CNP functions. Further, in some cases, a natriuretic polypeptide as provided herein can bind to and function through more than one guanylyl cyclase receptor, including NPR-A and NPR-B, for example. Methods for evaluating which receptor is involved in function of a particular natriuretic polypeptide are known in the art. For example, glomeruli, which contain both NPR-A and NPR-B, can be isolated (e.g., from a laboratory animal such as a dog) and incubated with a natriuretic polypeptide (e.g., a native, chimeric, or mutated natriuretic polypeptide), and cGMP levels can be measured. Glomeruli can be pretreated with antagonists of NPR-A or NPR-B to determine whether cGMP production stimulated by a natriuretic polypeptide through one or the other receptor can be attenuated.

In some cases, a compound (e.g., an isolated natriuretic polypeptide) provided herein can reduce or prevent restenosis. The presence or extent of restenosis can be evaluated using methods known in the art, including, for example, angiogram. In some cases, a compound (e.g., an isolated natriuretic polypeptide) provided herein can reduce or prevent cardiac remodeling. The term "cardiac remodeling" refers to effects on the heart that can occur with MI, acute heart failure (AHF), or other conditions. These include, for example, heart dilation, myocyte hypertrophy, and cardiofibrosis (i.e., proliferation of interstitial fibroblasts). The natriuretic polypeptides provided herein can inhibit or prevent cardiac remodeling that occurs with acute MI or AHF. In some embodiments, parameters indicative of reduced cardiac remodeling can include one or more of the following: cardiac unloading (i.e., reduced pressure in the heart), increased glomerular filtration rate (GFR), decreased plasma renin activity (PRA), decreased levels of angiotensin II, decreased proliferation of cardiac fibroblasts, decreased left ventricular (LV) hypertrophy), decreased LV mass (indicative of reduced fibrosis and hypertrophy), decreased pulmonary wedge capillary pressure (PWCP; an indirect measure of left atrial pressure), decreased right atrial pressure, decreased mean arterial pressure, decreased levels of aldosterone (indicative of an anti-fibrotic effect), decreased ventricular fibrosis, increased ejection fraction, and decreased LV end systolic diameter. To determine whether a natriuretic polypeptide is capable of inhibiting or reducing cardiac remodeling, one or more of these parameters can be evaluated (e.g., before and after treatment with the natriuretic polypeptide), using methods known in the art, for example.

Nucleic Acids, Vectors, and Host Cells

This document also describes exemplary nucleic acids encoding polypeptides (e.g., natriuretic polypeptides), as well as expression vectors containing the nucleic acids, and host cells containing the nucleic acids and/or expression vectors. As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids include, for example, cDNAs encoding the natriuretic polypeptides, variant natriuretic polypeptides, and chimeric natriuretic polypeptides provided herein.

An "isolated nucleic acid" is a nucleic acid that is separated from other nucleic acid molecules that are present in a vertebrate genome, including nucleic acids that normally flank one or both sides of the nucleic acid in a vertebrate genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid. By way of example and not limitation, an "isolated ANP nucleic acid," for example, can be a RNA or DNA molecule containing 9 or more (e.g., 15 or more, 21 or more, 36 or more, or 45 or more) sequential nucleotide bases that encode at least a portion of ANP, or a RNA or DNA complementary thereto.

Also provided herein are nucleic acid molecules that can selectively hybridize under stringent hybridization conditions to a nucleic acid molecule encoding a natriuretic polypeptide (e.g., a nucleic acid molecule encoding a polypeptide having the amino acid sequence set forth in any of SEQ ID NOS:3, 5, 6, 7, 8, 9, 10, 11, 12, or 13), or variants and fragments thereof. The term "selectively hybridize" means to detectably and specifically bind under hybridization and wash conditions that minimize appreciable amounts of detectable binding to nonspecific nucleic acids. For example, highly stringent or moderately stringent conditions can be used to achieve selective hybridization. Moderate and stringent hybridization conditions include those that are well known in the art. See, for example, sections 9.47-9.51 of Sambrook et al. (1989). For the purpose of this document, moderately stringent hybridization conditions mean the hybridization is performed at about 42° C. in a hybridization solution containing 25 mM $KPO_4$ (pH 7.4), 5×SSC, 5×Denhardt's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2×SSC and 0.1% sodium dodecyl sulfate. Highly stringent hybridization conditions mean the hybridization is performed at about 42° C. in a hybridization solution containing 25 mM $KPO_4$ (pH 7.4), 5×SSC, 5×Denhardt's solution, 50 µg/mL denatured, sonicated salmon sperm DNA, 50% formamide, 10% Dextran sulfate, and 1-15 ng/mL probe (about $5 \times 10^7$ cpm/m), while the washes are performed at about 65° C. with a wash solution containing 0.2×SSC and 0.1% sodium dodecyl sulfate.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing nucleotide sequence that encodes a natriuretic polypeptide as provided herein. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids (e.g., nucleic acids encoding variant natriuretic polypeptides) also can be obtained by mutagenesis. For example, a reference sequence can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Non-limiting examples of variant natriuretic polypeptides are provided herein.

This document also contemplates nucleic acid molecules encoding amino acid sequences from natriuretic polypeptides other than ANP, BNP, CNP, DNP, URO, or chimeras or variants thereof. Sources of nucleotide sequences from which nucleic acid molecules encoding a natriuretic polypeptide, or the nucleic acid complement thereof, can be obtained include total or polyA+ RNA from any eukaryotic source, including reptilian (e.g., snake) or mammalian (e.g., human, rat, mouse, canine, bovine, equine, ovine, caprine, or feline) cellular source from which cDNAs can be derived by methods known in the art. Other sources of the nucleic acid molecules provided herein include genomic libraries derived from any eukaryotic cellular source, including mammalian sources as exemplified above.

Nucleic acid molecules encoding native natriuretic polypeptides can be identified and isolated using standard methods, e.g., as described by Sambrook et al., *Molecular Cloning: A Laboratory Manual*, Cold Spring Harbor Laboratory Press, NY (1989). For example, reverse-transcriptase PCR (RT-PCR) can be used to isolate and clone natriuretic polypeptide cDNAs from isolated RNA that contains RNA sequences of interest (e.g., total RNA isolated from human tissue). Other approaches to identify, isolate and clone natriuretic polypeptide cDNAs include, for example, screening cDNA libraries.

Vectors containing nucleic acids such as those described herein also are provided. A "vector" is a replicon, such as a plasmid, phage, or cosmid, into which another DNA segment may be inserted so as to bring about the replication of the inserted segment. An "expression vector" is a vector that includes one or more expression control sequences, and an "expression control sequence" is a DNA sequence that controls and regulates the transcription and/or translation of another DNA sequence.

In the expression vectors provided herein, a nucleic acid (e.g., a nucleic acid encoding a natriuretic polypeptide) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence. Expression vectors thus can be useful to produce antibodies as well as other multivalent molecules.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

Host cells containing vectors also are provided. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Suitable methods for transforming and transfecting host cells can be found, for example, in Sambrook et al., *Molecular Cloning: A Laboratory Manual* ($2^{nd}$ edition), Cold Spring Harbor Laboratory, New York (1989). For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Detecting Polypeptides

This document provides methods and materials (e.g., antibodies) for detecting a polypeptide provided herein. Such methods and materials can be used to monitor polypeptide levels within a mammal receiving the polypeptide as a therapeutic. A natriuretic polypeptide provided herein can be detected, for example, immunologically, using one or more antibodies. As used herein, the term "antibody" includes intact molecules as well as fragments thereof that are capable of binding to an epitopic determinant of a polypeptide provided herein. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The term "antibody" includes polyclonal antibodies, monoclonal antibodies, humanized or chimeric antibodies, single chain Fv antibody fragments, Fab fragments, and $F(ab)_2$ fragments. Polyclonal antibodies are heterogeneous populations of antibody molecules that are contained in the sera of the immunized animals. Monoclonal antibodies are homogeneous populations of antibodies to a particular epitope of an antigen.

Antibody fragments that have specific binding affinity for a natriuretic polypeptide provided herein can be generated by known techniques. For example, F(ab')2 fragments can be produced by pepsin digestion of the antibody molecule; Fab fragments can be generated by reducing the disulfide bridges of F(ab')2 fragments. In some cases, Fab expression libraries can be constructed. See, for example, Huse et al., *Science*, 246:1275 (1989). Once produced, antibodies or fragments thereof can be tested for recognition of a polypeptide provided herein by standard immunoassay methods including ELISA techniques, radioimmunoassays, and Western blotting. See, *Short Protocols in Molecular Biology*, Chapter 11, Green Publishing Associates and John Wiley & Sons, Ed. Ausubel et al., 1992.

In immunological assays, an antibody having specific binding affinity for a polypeptide provided herein or a secondary antibody that binds to such an antibody can be labeled, either directly or indirectly. Suitable labels include, without limitation, radionuclides (e.g. $^{125}I$, $^{131}I$, $^{35}S$, $^{3}H$, $^{32}P$, $^{33}P$, or $^{14}C$), fluorescent moieties (e.g., fluorescein, FITC, PerCP, rhodamine, or PE), luminescent moieties (e.g., Qdot™ nanoparticles supplied by Invitrogen (Carlsbad, Calif.)), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting a polypeptide provided herein can be performed in a variety of known formats, including sandwich assays, competition assays (competitive RIA), or bridge immunoassays. See, for example, U.S. Pat.

Nos. 5,296,347; 4,233,402; 4,098,876; and 4,034,074. Methods of detecting a polypeptide provided herein generally include contacting a biological sample with an antibody that binds to a polypeptide provided herein and detecting binding of the polypeptide to the antibody. For example, an antibody having specific binding affinity for a polypeptide provided herein can be immobilized on a solid substrate by any of a variety of methods known in the art and then exposed to the biological sample. Binding of the polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). In some cases, the antibody can be labeled and detected as described above. A standard curve using known quantities of a polypeptide provided herein can be generated to aid in the quantitation of the levels of the polypeptide.

In some embodiments, a "sandwich" assay in which a capture antibody is immobilized on a solid substrate can be used to detect the presence, absence, or level of a polypeptide provided herein. The solid substrate can be contacted with the biological sample such that any polypeptide of interest in the sample can bind to the immobilized antibody. The presence, absence, or level of the polypeptide bound to the antibody can be determined using a "detection" antibody having specific binding affinity for the polypeptide. In some embodiments, a capture antibody can be used that has binding affinity for ANP, BNP, CNP, DNP, and/or URO, or a chimeric or variant polypeptide as described herein, and a detection antibody can be used that has specific binding affinity for a particular polypeptide provided herein (e.g., a polypeptide having the amino acid sequence set forth in any of SEQ ID NOS:3, 5, 6, 7, 8, 9, 10, 11, 12, or 13). It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for a polypeptide provided herein can be produced through standard methods. For example, a polypeptide can be recombinantly produced as described above, can be purified from a biological sample (e.g., a heterologous expression system), or can be chemically synthesized, and used to immunize host animals, including rabbits, chickens, mice, guinea pigs, or rats. For example, a polypeptide having the amino acid sequence set forth in any of SEQ ID NOS:3, 5, 6, 7, 8, 9, 10, 11, 12, or 13, or fragments or variants thereof that are at least six amino acids in length, can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a polypeptide provided herein and standard hybridoma technology. In particular, monoclonal antibodies can be obtained by any technique that provides for the production of antibody molecules by continuous cell lines in culture such as described by Kohler et al., Nature, 256:495 (1975), the human B-cell hybridoma technique (Kosbor et al., Immunology Today, 4:72 (1983); Cote et al., Proc. Natl. Acad. Sci. USA, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

Other techniques for detecting a polypeptide provided herein include mass-spectrophotometric techniques such as electrospray ionization (ESI), and matrix-assisted laser desorption-ionization (MALDI). See, for example, Gevaert et al., Electrophoresis, 22:1645-51 (2001); Chaurand et al., J. Am. Soc. Mass Spectrom., 10:91-103 (1999). Mass spectrometers useful for such applications are available from Applied Biosystems (Foster City, Calif.); Bruker Daltronics (Billerica, Mass.); and Amersham Pharmacia (Sunnyvale, Calif.).

Methods for Diagnosing or Determining Predisposition to Arrhythmias

This document also provides methods for determining whether a mammal has or is predisposed to develop a cardiac arrhythmia such as atrial fibrillation, for example. The methods can include, for example, obtaining a biological sample (e.g., blood, serum, urine, cerebrospinal fluid, pleural fluid, sputum, peritoneal fluid, bladder washings, oral washings, tissue samples, touch preps, or fine-needle aspirates) from a mammal and assaying the sample to determine whether or not it contains a polypeptide that includes the amino acid sequence set forth in SEQ ID NO:13 herein, or a nucleic acid encoding such an amino acid sequence. In some embodiments, the method can include determining whether or not the sample contains a polypeptide including the amino acid sequence set forth in SEQ ID NO:13, but with less than five (e.g., four, three, two, one) amino acid additions, subtractions, and substitutions relative to SEQ ID NO:13. If the sample is determined to contain the polypeptide or nucleic acid, the mammal can be diagnosed as having, or predisposed to develop, a cardiac arrhythmia such as atrial fibrillation, for example.

Any suitable method can be used to determine whether a biological sample contains a polypeptide that includes the amino acid sequence set forth in SEQ ID NO:13, or an amino acid sequence having less than five amino acid additions, subtractions, and substitutions relative to SEQ ID NO:13. For example, the methods described herein for detecting polypeptides (e.g., antibody-based methods using an antibody directed to SEQ ID NO:13) can be used to determine whether a biological sample contains a polypeptide that include the amino acid sequence of SEQ ID NO:13.

Methods for detecting nucleic acids include those known in the art. For example, DNA sequencing, PCR-based techniques, or hybridization-based methods can be used to determine whether a biological sample from a mammal contains a nucleic acid that encodes a polypeptide containing the amino acid sequence set forth in SEQ ID NO:13, or an amino acid sequence having less than five (e.g., four, three, two, or one) amino acid additions, subtractions, and substitutions relative to SEQ ID NO:13. Nucleic acid sequences can be detected, for example, by sequencing the NPPA gene, by performing allele-specific hybridization, allele-specific restriction digests, mutation specific polymerase chain reactions (MSPCR), by single-stranded conformational polymorphism (SSCP) detection (Schafer et al. (1995) Nat. Biotechnol. 15:33-39), denaturing high performance liquid chromatography (DHPLC, Underhill et al. (1997) Genome Res. 7:996-1005), infrared matrix-assisted laser desorption/ionization (IR-MALDI) mass spectrometry (WO 99/57318), and combinations of such methods.

Genomic DNA generally is used in the analysis of NPPA nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAAMP® Tissue Kit (Qiagen, Chatsworth, Calif.), WIZARD® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons of the NPPA gene can be amplified and then directly sequenced. Dye primer sequencing can be used to increase the accuracy of detecting heterozygous samples.

Nucleic acid molecules provided herein can be used to detect variant PPNA sequences. For example, allele specific hybridization also can be used to detect sequence variants, including complete haplotypes of a subject (e.g., a mammal such as a human). See, Stoneking et al. (1991) Am. J. Hum. Genet. 48:370-382; and Prince et al. (2001) Genome Res. 11:152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency conditions as defined herein, although moderately stringent conditions also may be useful. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For PPNA sequence variants that do not alter a common restriction site, mutagenic primers can be designed that introduce a restriction site when the variant allele is present or when the wild type allele is present. A portion of PPNA nucleic acid can be amplified using the mutagenic primer and a wild type primer, followed by digest with the appropriate restriction endonuclease.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader. See, Myakishev et al. (2001) Genome 11:163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Methods for determining diagnosis of or predisposition to cardiac arrhythmia also can include assisting medical or research professionals in determining whether or not a mammal has or is predisposed to develop cardiac arrhythmia (e.g., atrial fibrillation). Medical professionals can be, for example, doctors, nurses, medical laboratory technologists, and pharmacists. Research professionals can be, for example, principle investigators, research technicians, postdoctoral trainees, and graduate students. A professional can be assisted by (1) determining whether a biological sample from a mammal contains a polypeptide that includes the amino acid sequence of SEQ ID NO:13 (or a polypeptide having a sequence with less than five amino acid amino acid additions, subtractions, and substitutions relative to SEQ ID NO:13), or a nucleic acid encoding such a polypeptide, and (2) communicating information about the polypeptide to that professional.

After information regarding the presence or absence of a polypeptide as described above is reported, a medical professional can take one or more actions that can affect patient care. For example, a medical professional can record the level of a polypeptide in a patient's medical record. In some cases, a medical professional can record a diagnosis of or predisposition to arrhythmia or fibrillation, or otherwise transform the patient's medical record, to reflect the patient's medical condition. In some cases, a medical professional can review and evaluate a patient's entire medical record, and assess multiple treatment strategies, for clinical intervention of a patient's condition.

A medical professional can initiate or modify treatment for arrhythmia after receiving information regarding a patient's polypeptide levels. In some cases, a medical professional can compare previous reports of polypeptide levels with the recently communicated polypeptide level, and recommend a change in therapy. In some cases, a medical professional can enroll a patient in a clinical trial for novel therapeutic intervention of cardiac arrhythmia. In some cases, a medical professional can elect waiting to begin therapy until the patient's symptoms require clinical intervention.

A medical professional can communicate the levels of a polypeptide to a patient or a patient's family. In some cases, a medical professional can provide a patient and/or a patient's family with information regarding arrhythmias, including treatment options, prognosis, and referrals to specialists, e.g., cardiologists. In some cases, a medical professional can provide a copy of a patient's medical records to communicate the levels of a polypeptide to a specialist.

A research professional can apply information regarding a subject's polypeptide levels to advance research into cardiac arrhythmias. For example, a researcher can compile data on polypeptide levels with information regarding the efficacy of a drug for treatment of atrial fibrillation to identify an effective treatment. In some cases, a research professional can obtain a subject's polypeptide levels to evaluate a subject's enrollment, or continued participation in a research study or clinical trial. In some cases, a research professional can classify the severity of a subject's condition, based on the levels of a polypeptide. In some cases, a research professional can communicate a subject's polypeptide level to a medical professional. In some cases, a research professional can refer a subject to a medical professional for clinical assessment and treatment of arrhythmia symptoms.

Any appropriate method can be used to communicate information to another person (e.g., a professional). For example, information can be given directly or indirectly to a professional. For example, a laboratory technician can input polypeptide levels into a computer-based record. In some cases, information is communicated by making an physical alteration to medical or research records. For example, a medical professional can make a permanent notation or flag a medical record for communicating a diagnosis to other medical professionals reviewing the record. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

Compositions and Methods for Administration

The compounds described herein (e.g., native natriuretic polypeptides, as well as chimeric and variant natriuretic polypeptides), or nucleic acids encoding the polypeptides described herein, can be incorporated into compositions for administration to a subject (e.g., a subject suffering from or at risk for an arrhythmia, such as fibrillation). Methods for formulating and subsequently administering therapeutic compositions are well known to those in the art. Dosages typically are dependent on the responsiveness of the subject to the compound, with the course of treatment lasting from several days to several months, or until a suitable response is achieved. Persons of ordinary skill in the art routinely determine optimum dosages, dosing methodologies and repetition rates. Optimum dosages can vary depending on the relative potency of an antibody, and generally can be estimated based on the $EC_{50}$ found to be effective in in vitro and/or in vivo animal models. Compositions containing the compounds (e.g., natriuretic polypeptides) and nucleic acids provided herein may be given once or more daily, weekly, monthly, or even less often, or can be administered continuously for a period of time (e.g., hours, days, or weeks). For example, a natriuretic polypeptide or a composition containing a natriuretic polypeptide can be administered to a patient at a dose of at least about 0.01 ng natriuretic polypeptide/kg to about 100 mg natriuretic polypeptide/kg of body mass at or about the time of reperfusion, or can be administered continuously as an infusion beginning at or about the time of reperfusion and continuing for one to seven days (e.g., at a dose of about 0.01 ng natriuretic polypeptide/kg/minute to about 0.5 µg natriuretic polypeptide/kg/minute).

The natriuretic polypeptides and nucleic acids can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

In some embodiments, a composition can contain a natriuretic polypeptide as provided herein in combination with a pharmaceutically acceptable carrier. Pharmaceutically acceptable carriers include, for example, pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing molecules described herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful. In some embodiments, transdermal delivery of natriuretic polypeptides as provided herein can be particularly useful. Methods and compositions for transdermal delivery include those described in the art (e.g., in Wermeling et al. (2008) *Proc. Natl. Acad. Sci. USA* 105:2058-2063; Goebel and Neubert (2008) *Skin Pharmacol. Physiol.* 21:3-9; Banga (2007) *Pharm. Res.* 24:1357-1359; Malik et al. (2007) *Curr. Drug Deliv.* 4:141-151; and Prausnitz (2006) *Nat. Biotechnol.* 24:416-417). Nasal preparations can be presented in a liquid form or as a dry product.

Nebulized aqueous suspensions or solutions can include carriers or excipients to adjust pH and/or tonicity.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Compositions provided herein can contain any pharmaceutically acceptable salts, esters, or salts of such esters, or any other compound which, upon administration to a subject, is capable of providing (directly or indirectly) the biologically active metabolite or residue thereof for the relevant compound (e.g., natriuretic polypeptide). Accordingly, for example, this document describes pharmaceutically acceptable salts of natriuretic polypeptides, prodrugs and pharmaceutically acceptable salts of such prodrugs, and other bioequivalents. A prodrug is a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the natriuretic polypeptides useful in methods provided herein (i.e., salts that retain the desired biological activity of the parent natriuretic polypeptides without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the other components within the compositions.

In some cases, a polypeptide provided herein can be formulated as a sustained release dosage form. For example, a natriuretic polypeptide can be formulated into a controlled release formulation. In some cases, coatings, envelopes, or protective matrices can be formulated to contain one or more of the polypeptides provided herein. Such coatings, envelopes, and protective matrices can be used to coat indwelling devices such as stents, catheters, and peritoneal dialysis tubing. In some cases, a polypeptide provided herein can incorporated into a polymeric substances, liposomes, microemulsions, microparticles, nanoparticles, or waxes.

Pharmaceutical formulations as disclosed herein, which can be presented conveniently in unit dosage form, can be prepared according to conventional techniques well known in the pharmaceutical industry. Such techniques include the step of bringing into association the active ingredients (i.e., the antibodies) with the desired pharmaceutical carrier(s). Typically, the formulations can be prepared by uniformly and intimately bringing the active ingredients into association with liquid carriers or finely divided solid carriers or both, and then, if necessary, shaping the product. Formulations can be sterilized if desired, provided that the method of sterilization does not interfere with the effectiveness of the molecules(s) contained in the formulation.

Methods for Treating Cardiac Arrhythmias

This document also provides methods for using compounds (e.g., natriuretic polypeptides) as disclosed herein for cardiac arrhythmias. In some embodiments, for example, the compounds and nucleic acid molecules described herein can be administered to a mammal (e.g., a human or a non-human mammal) to treat cardiovascular conditions such as atrial fibrillation. The composition or natriuretic polypeptide can be administered at any suitable dose, depending on various factors including, without limitation, the agent chosen and the patient characteristics. Administration can be local or systemic.

In some embodiments, a natriuretic polypeptide or a composition containing a natriuretic polypeptide can be administered at a dose of at least about 0.01 ng natriuretic polypeptide/kg to about 100 mg natriuretic polypeptide/kg of body mass (e.g., about 10 ng natriuretic polypeptide/kg to about 50 mg natriuretic polypeptide/kg, about 20 ng natriuretic polypeptide/kg to about 10 mg natriuretic polypeptide/kg, about 0.1 ng natriuretic polypeptide/kg to about 20 ng natriuretic polypeptide/kg, about 3 ng natriuretic polypeptide/kg to about 10 ng natriuretic polypeptide/kg, or about 50 ng natriuretic polypeptide/kg to about 100 µg/kg) of body mass, although other dosages also may provide beneficial results. A composition can be administered at a dose of, for example, about 0.1 ng natriuretic polypeptide/kg/minute to about 500 ng natriuretic polypeptide/kg/minute (e.g., about 0.5 ng natriuretic polypeptide/kg/minute, about 1 ng natriuretic polypeptide/kg/minute, about 2 ng natriuretic polypeptide/kg/minute, about 3 ng natriuretic polypeptide/kg/minute, about 5 ng natriuretic polypeptide/kg/minute, about 7.5 ng natriuretic polypeptide/kg/minute, about 10 ng natriuretic polypeptide/kg/minute, about 12.5 ng natriuretic polypeptide/kg/minute, about 15 ng natriuretic polypeptide/kg/minute, about 20 ng natriuretic polypeptide/kg/minute, about 25 ng natriuretic polypeptide/kg/minute, about 30 ng natriuretic polypeptide/kg/minute, about 50 ng natriuretic polypeptide/kg/minute, about 100 ng natriuretic polypeptide/kg/minute, or about 300 ng natriuretic polypeptide/kg/minute).

In some embodiments, a natriuretic polypeptide or a composition containing a natriuretic polypeptide can be administered via a first route (e.g., intravenously) for a first period of time, and then can be administered via another route (e.g., topically or subcutaneously) for a second period of time. For example, a composition containing a natriuretic polypeptide can be intravenously administered to a mammal (e.g., a human) at a dose of about 0.1 ng natriuretic polypeptide/kg/minute to about 300 ng natriuretic polypeptide/kg/minute (e.g., about 1 ng natriuretic polypeptide/kg/minute to about 15 ng natriuretic polypeptide/kg/minute, about 3 ng natriuretic polypeptide/kg/minute to about 10 ng natriuretic polypeptide/kg/minute, or about 10 ng natriuretic polypeptide/kg/minute to about 30 ng natriuretic polypeptide/kg/minute) for one to seven days (e.g., one, two, three, four, five, six, or seven days), and subsequently can be subcutaneously administered to the mammal at a dose of about 10 ng natriuretic polypeptide/kg/day to about 100 ng natriuretic polypeptide/kg/day (e.g., about 10 ng natriuretic polypeptide/kg/day, about 20 ng natriuretic polypeptide/kg/day, about 25 ng natriuretic polypeptide/kg/day, about 30 ng natriuretic polypeptide/kg/day, about 50 ng natriuretic polypeptide/kg/day, or about 100 ng natriuretic polypeptide/kg/day) for five to 30 days (e.g., seven, 10, 14, 18, 21, 24, or 27 days).

The methods provided herein can include administering to a mammal an effective amount of a natriuretic polypeptide (e.g., a native, chimeric, or variant natriuretic polypeptide) or a nucleic acid encoding a natriuretic polypeptide, or an effective amount of a composition containing such a molecule. As used herein, the term "effective amount" is an amount of a molecule or composition that is sufficient to alter the desired parameter by at least 10%. For example, in some embodiments, an "effective amount" of a natriuretic polypeptide can be an amount of the natriuretic polypeptide that is sufficient to increase natriuresis and/or diuresis (or a characteristic of natriuresis and/or diuresis such as plasma cGMP levels, urinary cGMP excretion, net renal cGMP generation, urine flow, urinary sodium excretion, urinary potassium excretion, hematocrit, plasma BNP immunoreactivity, renal blood flow, plasma ANP immunoreactivity, renal vascular resistance, proximal and distal fractional reabsorption of sodium, mean arterial pressure, pulmonary capillary wedge pressure, right atrial pressure, pulmonary arterial pressure, plasma renin activity, plasma angiotensin II levels, plasma aldosterone levels, renal perfusion pressure, and systemic vascular resistance) by at least 10% (e.g., 10%, 15%, 20%, 25%, 30%, 40%, 50%, 60%, 70%, 75%, 80%, 85%, 90%, 95%, 99%, or 100%). For example, an "effective amount" of a natriuretic polypeptide can be an amount that increases sodium excretion in a treated mammal by at least 10% as compared to the level of sodium excretion in the mammal prior to administration of the natriuretic polypeptide, or as compared to the level of sodium excretion in a control, untreated mammal.

In some embodiments, an "effective amount" of a natriuretic polypeptide can be an amount of the natriuretic polypeptide that is sufficient to reduce the occurrence of fibrillation in a mammalian recipient by at least 10% (e.g., 10%, 15%, 20%, 25%, 30%, 40%, 50%, 60%, 70%, 75%, 80%, 85%, 90%, 95%, 99%, or 100%). In some cases, for example, an "effective amount" of a natriuretic polypeptide as provided herein can be an amount that reduces atrial fibrillation in a treated mammal by at least 10% as compared to the level of atrial fibrillation in the mammal prior to administration of the natriuretic polypeptide or without administration of the natriuretic polypeptide, or as compared to the level of atrial fibrillation in a control, untreated mammal. The presence or extent of atrial fibrillation can be evaluated using methods known in the art, including, for example, electrocardiography.

Before administering a composition provided herein to a mammal, the mammal can be assessed to determine whether or not the mammal has a need for treatment of an arrhythmia (e.g., a patient having atrial fibrillation). After identifying a mammal as having an arrhythmia, the mammal can be treated with a composition provided herein. For example, a composition containing one or more polypeptides having a natriuretic polypeptide activity can be administered to a mammal in any amount, at any frequency, and for any duration effective to achieve a desired outcome (e.g., to reduce atrial fibrillation).

In some embodiments, the amount and frequency of natriuretic polypeptide administered to a mammal can be titrated in order to, for example, identify a dosage that is most effective to correct an arrhythmia while having the least amount of adverse effects. For example, an effective amount of a composition can be any amount that reduces fibrillation within a mammal without having significant toxicity in the mammal. If a particular mammal fails to respond to a particular amount, then the amount can be increased by, for example, ten fold. After receiving this higher concentration, the mammal can be monitored for both responsiveness to the treatment and toxicity symptoms, and adjustments in the dosage can be made accordingly. The effective amount can remain constant or can be adjusted as a sliding scale or variable dose depending on the mammal's response to treatment.

The frequency of administration can be any frequency that reduces arrhythmia within a mammal without producing significant toxicity in the mammal. For example, the frequency of administration can be from about four times a day to about once every other month, or from about once a day to about once a month, or from about once every other day to about once a week. In addition, the frequency of administration can remain constant or can be variable during the duration of treatment. As with the effective amount, various factors can influence the actual frequency of administration used for a particular application. For example, the effective amount, duration of treatment, route of administration, and severity of renal condition may require an increase or decrease in administration frequency.

An effective duration of administration can be any duration that reduces arrhythmia within a mammal without producing significant toxicity in the mammal. The effective duration can vary from several days to several weeks, months, or years. In general, the effective duration for can range in duration from several days to several months. For example, an effective duration can range from about one to two weeks to about 36 months. Prophylactic treatments can be typically longer in duration and can last throughout an individual mammal's lifetime. Multiple factors can influence the actual effective duration used for a particular treatment or prevention regimen. For example, an effective duration can vary with the frequency of administration, amount administered, route of administration, and severity of a renal condition.

After administering a composition provided herein to a mammal, the mammal can be monitored to determine whether cardiac rhythm has been improved. For example, a mammal can be assessed after treatment to determine whether or not arrhythmia has been reduced. As described herein, any method can be used to assess improvements in cardiac rhythm.

The invention will be further described in the following examples, which do not limit the scope of the invention described in the claims.

EXAMPLES

Example 1 mANP and Clinical Effects

Methods

Figure 2:
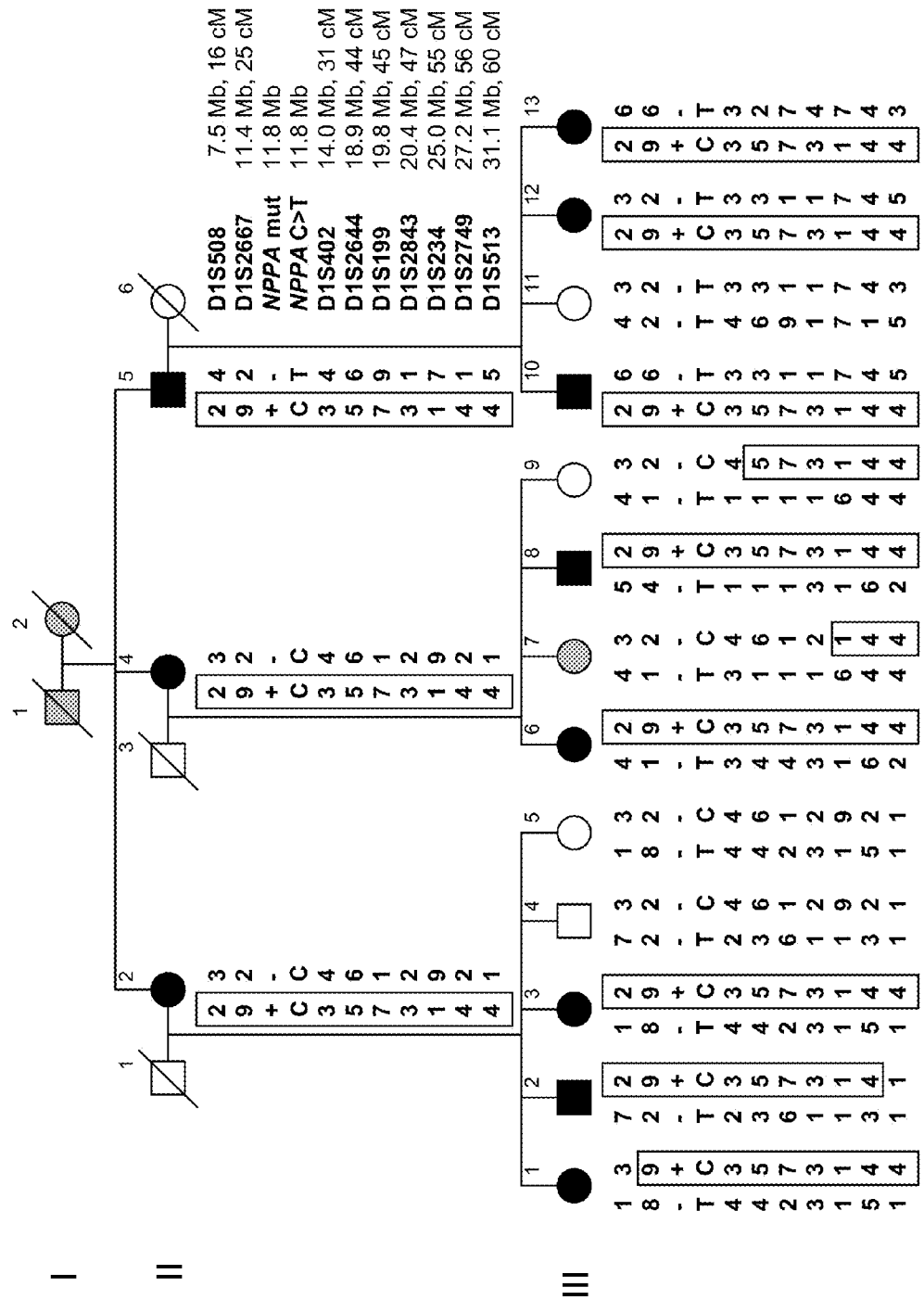
FIG. 2 is a diagram of a pedigree of a family with hereditary atrial fibrillation. Family members are identified by generation (Roman numerals) and by order within the generation (Arabic numerals). The pedigree symbols are as follows: squares, male; circles, female; black, affected; white, unaffected; gray, uncertain; slash, deceased. The gene for atrial natriuretic peptide (NPPA) is located at 1p36-p35. Markers tested for this region of chromosome 1 are listed in order from the p-terminal end of the chromosome, with map locations according to the National Center for Biotechnology Information website (World Wide Web at. ncbi.nlm.nih.gov) given in megabases (Mb) and centiMorgans (cM). A common 454 C>T polymorphism in exon 3 of wild-type NPPA is included, as is the mutation identified herein as NPPA mut. The haplotypes for these markers are shown in columns beneath each family member who had a genetic evaluation; the disease-associated haplotype is boxed. Two individuals (111.7 and 111.9) inherited portions of the disease haplotype, but not the disease gene, as a result of recombination events.

Study Subjects:

A Caucasian family of northern European ancestry with atrial fibrillation segregating as an autosomal dominant trait was studied (FIG. 2). In addition, a group of normal control individuals was randomly selected from a population-based cohort of northern European Caucasians with normal electrocardiograms and echocardiograms.

Medical records for all of the study participants were reviewed. Phenotypic classification as "affected" required documentation of atrial fibrillation on an electrocardiographic tracing and absence of clinical risk factors for arrhythmia, such as uncontrolled hypertension or primary structural heart disease. Individuals with a normal electrocardiogram who lacked symptoms of frequent palpitations, racing heart rate, dizziness, or syncope were classified as "unaffected."

For genetic analysis, genomic DNA was isolated from peripheral white blood cells. For protein studies, three family members consented to procurement of an additional blood sample; samples were collected in EDTA tubes and centrifuged at 2500 rpm (4° C.) for 10 minutes.

Linkage Analysis and Mapping:

The ABI PRISM Linkage Mapping Set-v2.5 MD10 (Applied Biosystems, Foster City, Calif.) was utilized for primary genome scanning, which included fluorescently labeled PCR primer pairs for 400 tandem repeat markers with an average spacing of 10 centiMorgans. Following PCR amplification of genomic DNA samples, amplified fragments were resolved on an ABI PRISM 3100 Genetic Analyzer and analyzed with GeneScan Analysis and Genotyper Software. Two-point and multipoint linkage analyses were performed using the FASTLINK program, specifying the following parameters: disease allele frequency 0.001, phenocopy rate 0.001, equal marker allele frequencies, and dichotomous liability classes ("affected" and "unaffected"). Lod scores were determined for affecteds-only, 80%, and 100% penetrance models at recombination frequencies of 0.0 to 0.4.

Fine mapping utilized additional closely spaced microsatellite markers localized on genetic and physical maps accessible at the NCBI website (World Wide Web at ncbi.nlm.nih.gov). Genotyping was accomplished by PCR amplification of genomic DNA radiolabeled with alpha-($^{32}$P)-dCTP, resolution of alleles by polyacrylamide gel electrophoresis, and visualization by autoradiography. Scored genotypes were assembled as haplotypes to define the critical region of complete linkage, based on recombination events in affected individuals.

Mutation Detection:

Primer pairs for exon-specific PCR amplification of the three translated exons of the gene encoding ANP were designed using OLIGO v6.51 Primer Analysis Software (National Biosciences, Plymouth, Minn.). Sequences for the primer pairs were as follows:

```
                                          (SEQ ID NO: 25)
NPPA exon 1F:  5'-GGAGACAGGGACAGACGTAG-3'

(SEQ ID NO: 26)
NPPA exon 1R:  5'-CCCAGACTGCACCCGCTTTC-3'

(SEQ ID NO: 27)
NPPA exon 2F:  5'-GCCAGGAAAGCGGGTGCAG-3'

(SEQ ID NO: 28)
NPPA exon 2R:  5'-GGGCACTCTGGGTGTTGGG-3'

(SEQ ID NO: 29)
NPPA exon 3F:  5'-GTGGGAAGCAGGTGGTCAGTA-3'

(SEQ ID NO: 30)
NPPA exon 3R:  5'-AGCTTAGATGGGATGATCACA-3'
```

Amplified products were treated with the PCR Product Pre-sequencing Kit (USB Corporation) and sequenced by the dye-terminator method using an ABI PRISM 3730 XL DNA Analyzer (Applied Biosystems). DNA sequences were viewed and analyzed using the Sequencher computer program (Gene Codes Corporation, Ann Arbor, Mich.), and a mutation was identified that segregated with atrial fibrillation. For single-allele sequencing of DNA from heterozygotes, the mutant allele was separated from the wild-type allele by polyacrylamide gel electrophoresis. Normal control samples were screened for the mutation by denaturing high-performance liquid chromatography heteroduplex analysis, using the WAVE DNA Fragment Analysis System (Transgenomic, Omaha, Nebr.).

Mutant ANP Peptide and Antibody:

A custom-designed polyclonal antibody against the mutant form of ANP (mANP) was manufactured commercially (21$^{st}$ Century Biochemicals, Marlboro, Mass.). The peptide Ac-CYRITAREDKQGWA-OH (SEQ ID NO:31), corresponding to the anomalous residues of mutant ANP, was synthesized, HPLC-purified to 96%, and verified by peptide sequencing and mass spectroscopy. Conjugated peptide was injected into rabbits, serving as an epitope for the generation of affinity-purified polyclonal antibody. Full-length (40-amino acid) mANP was synthesized in a core facility for use in developing the mANP radioimmunoassay and for the isolated heart experiments.

Radioimmunoassay:

Radioimmunoassays were developed for both mANP (using the polyclonal antibody described above) and for wild-type ANP (using commercially available antibody, Phoenix Pharmaceuticals, Burlingame, Calif.; Cat. #005-06). Both antibodies were labeled with $I^{125}$. C-18 Bond Elution cartridges were pre-washed with 4 ml 100% methanol and 4 ml water, after which 1 ml of plasma was applied. Cartridges with adsorbed peptides were then washed with 2 ml saline, 6 ml water, and 1 ml 100% methanol. ANP and mANP were eluted with 2 ml 75% methanol and 1% TFA. Eluates were dried and concentrated overnight on a Savant speed vacuum and re-suspended in 300 µl assay buffer. 100 µl of samples and standards were incubated with 100 µl diluted (1:150,000) anti-human ANP or anti-mANP at 4° C. After 18 hours, 100 µl (10,000 counts) $I^{125}$-labelled ANP or mANP was added and incubated at 4° C. for 18 hours. A secondary antibody was then added to each sample, followed by centrifugation to separate free and bound fractions. The free fraction was aspirated and the bound fraction was counted on a gamma counter.

Binding specificity of anti-mANP antibody was demonstrated by first generating standard curves with varying amounts of synthetic mANP, then performing measurements of patient samples at several dilutions to assess cross-reactivity. Standard curves were generated for calculating the ANP and mANP concentrations in pg/ml for both the patient and control samples. The range of the standard curve was 2 to 500 pg/ml for both ANP and mANP. All peptide measurements were made in duplicate and values were reported as the average of the two. The normal range for ANP using this assay was determined to be 25±11 pg/ml (n=100).

A commercially available immuno-radiometric assay was used to measure BNP concentrations (Shionogi and Co., Ltd., Osaka, Japan). For BNP assays, standard solutions or patient plasma samples (100 µl) were incubated with a monoclonal antibody that was specific for the carboxyl-terminal region of BNP and bound to solid beads. A second $I^{125}$-labeled monoclonal antibody (200 µl) specific for the ring structure of BNP was added to form a sandwich complex. After 14-18 hours of incubation at 4° C., the beads were washed to remove the unbound radio-iodinated antibody and the bound fraction was counted on a gamma counter.

A calibration curve (range 0 to 2000 pg/ml) was constructed from standard BNP solutions to estimate BNP concentrations of the samples. The normal range for BNP using this assay was determined to be 12±4 pg/ml (n=100).

Isolated Heart Model:

Atrial monophasic action potentials and effective refractory periods were measured in isolated perfused hearts obtained from male rats. Rapid cardiectomy was performed in male rats weighing 300-350 g, under general anesthesia with pentobarbital. The hearts were retrogradely perfused via the aorta at constant pressure and temperature (100 mmHg and 37° C.) with Kreb's-Henseleit buffer filtered at 0.22 µm and bubbled with 95% $O_2$/5% $CO_2$ at 37° C. and pH 7.4. Coronary perfusion flow was monitored constantly (T402, Transonic Systems, Ithaca, N.Y.) and remained >10 ml/min.

After establishment of a stable perfused heart preparation, the posterior atria were cut away to expose the left and right atrial endocardium and the atrioventricular (AV) node was mechanically crushed, resulting in AV dissociation. The right atrium was paced (Bloom Electrophysiology, via Fischer Imaging, Denver, Colo.) at a cycle length of 150 msec with a 0.1 msec pulse width using a bipolar platinum-tipped electrode (NuMED, Inc., Hopkinton, N.Y.), while the right ventricle was paced at a cycle length of 500 msec. A monophasic action potential (MAP) probe (Harvard Apparatus, Holliston, Mass.) was maintained in a single position on the anterior left atrial endocardium. Amplified signals (IsoDam, World Precision Instruments, Sarasota, Fla.) were digitally acquired at 2 kHz (USB-6210 and LabVIEW 8.2, National Instruments, Austin, Tex.). The MAP duration was measured at 90% repolarization on atrial beats without far field ventricular interference. The effective refractory period (ERP) was measured by delivering extrastimuli via the pacing catheter at decremental coupling intervals following at least 8 beats of a 150 ms cycle-length drive train. The ERP was determined as the longest extrastimulus coupling interval that failed to result in a propagated response as measured by the left atrial MAP probe. In separate heart preparations, the perfusion buffer was supplemented after baseline data acquisition with 100 nM of either ANP or mANP to assess the effect of both the wild-type and mutant hormones on MAP duration and ERP.

A two-sided t-test was used for comparison of data, assuming equal variance. Data are expressed as mean±S.E., and results were considered significant at p<0.05.

Results

Clinical data were collected on 16 members of the study family (FIG. 2 and Table 2). Eleven affected family members were diagnosed at a mean age of 40 years, three during pregnancy. Transition from paroxysmal to chronic atrial fibrillation (n=3) or to arrest of atrial activation (n=4) suggested progressive electrical remodeling. Five family members presented with tachycardia-induced cardiomyopathy, which improved or resolved with effective pharmacological rate control. Subsequent echocardiography excluded cardiac hypertrophy and contractile dysfunction, but demonstrated dilation of left atrial (n=7) and ventricular (n=4) chambers.

Genome-wide linkage analyses excluded known loci for atrial fibrillation and identified peak two-point lod scores at marker D1S2667, ranging from 2.32 (affecteds-only analysis) to 3.56 (100% penetrance) at a recombination frequency of 0%. Fine mapping defined a disease-associated haplotype on chromosome 1p36-p35, a region spanning 24 Mb, inherited by all affected individuals (peak multi-point lod scores=2.66 for affecteds-only and 3.90 for 100% penetrance; FIG. 2). A recombination event within this interval in a 38 year-old asymptomatic male (III.9), if he was assumed to be unaffected, further narrowed the critical region to 11 Mb.

Figure 1B:
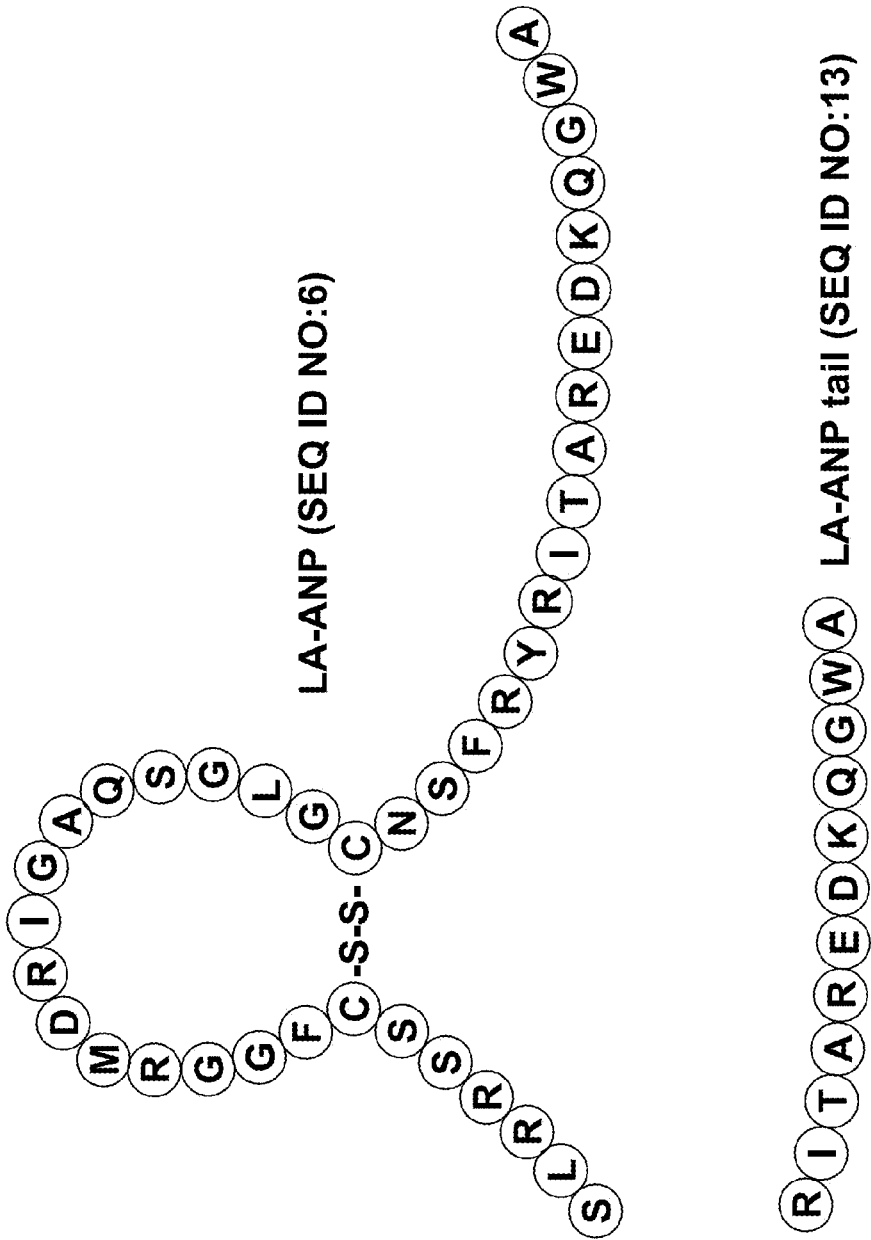
Figure 5A:
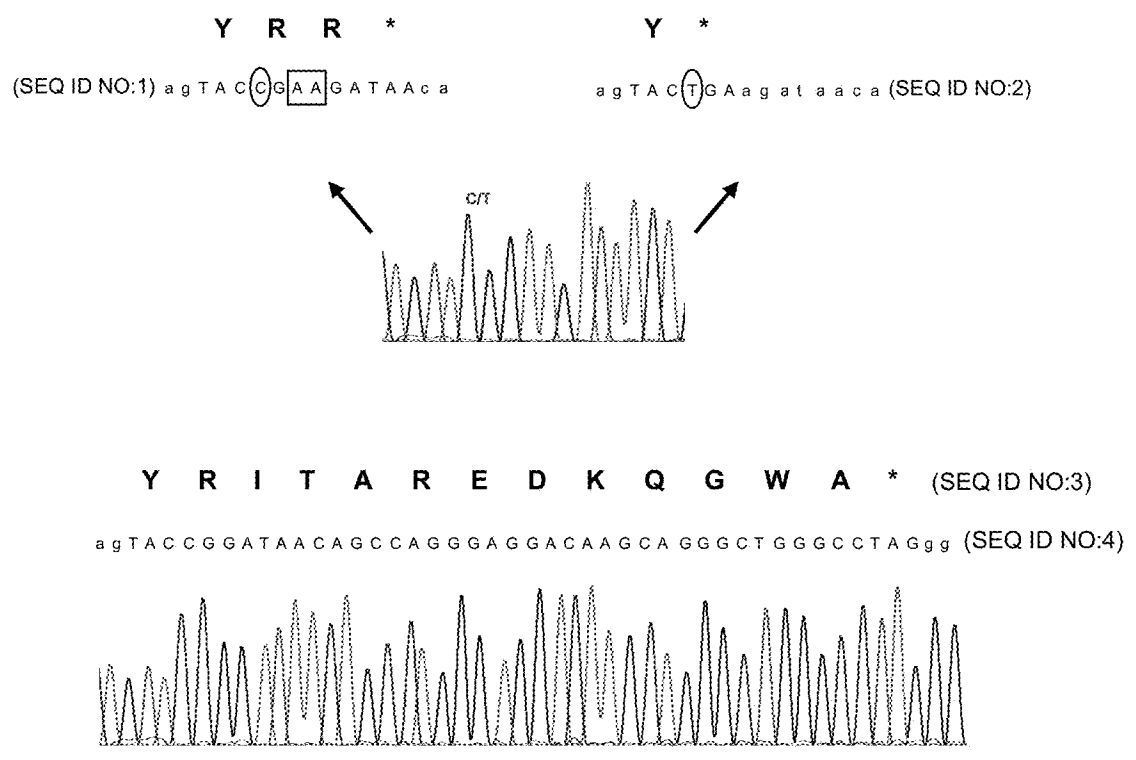

The gene encoding ANP (NPPA) was selected as a candidate gene based on its localization in the mapped interval, its expression in the atria of the heart and its established role in cardiovascular physiology (Burnett et al. (1986) *Science* 231: 1145-1147; and Levin et al. (1998) *N. Engl. J. Med.* 339:321-328). Seven other genes were excluded, including two (SLC9A1 and CLIC4) with direct roles in ion regulation. Genomic DNA sequencing of NPPA identified a 2-base-pair deletion (456-457delAA) in exon 3 that causes a frameshift, which abolishes the stop codon and extends the reading frame. Translation of the mutant gene would generate a fusion protein comprising the normal 28-amino acid mature peptide plus an anomalous carboxyl-terminus of 12 residues (FIGS. 1B and 5B). Each of the 11 clinically affected family members was heterozygous for the mutation; the mutation was absent in the other 5 family members and in 560 normal Caucasian controls.

Figure 3:
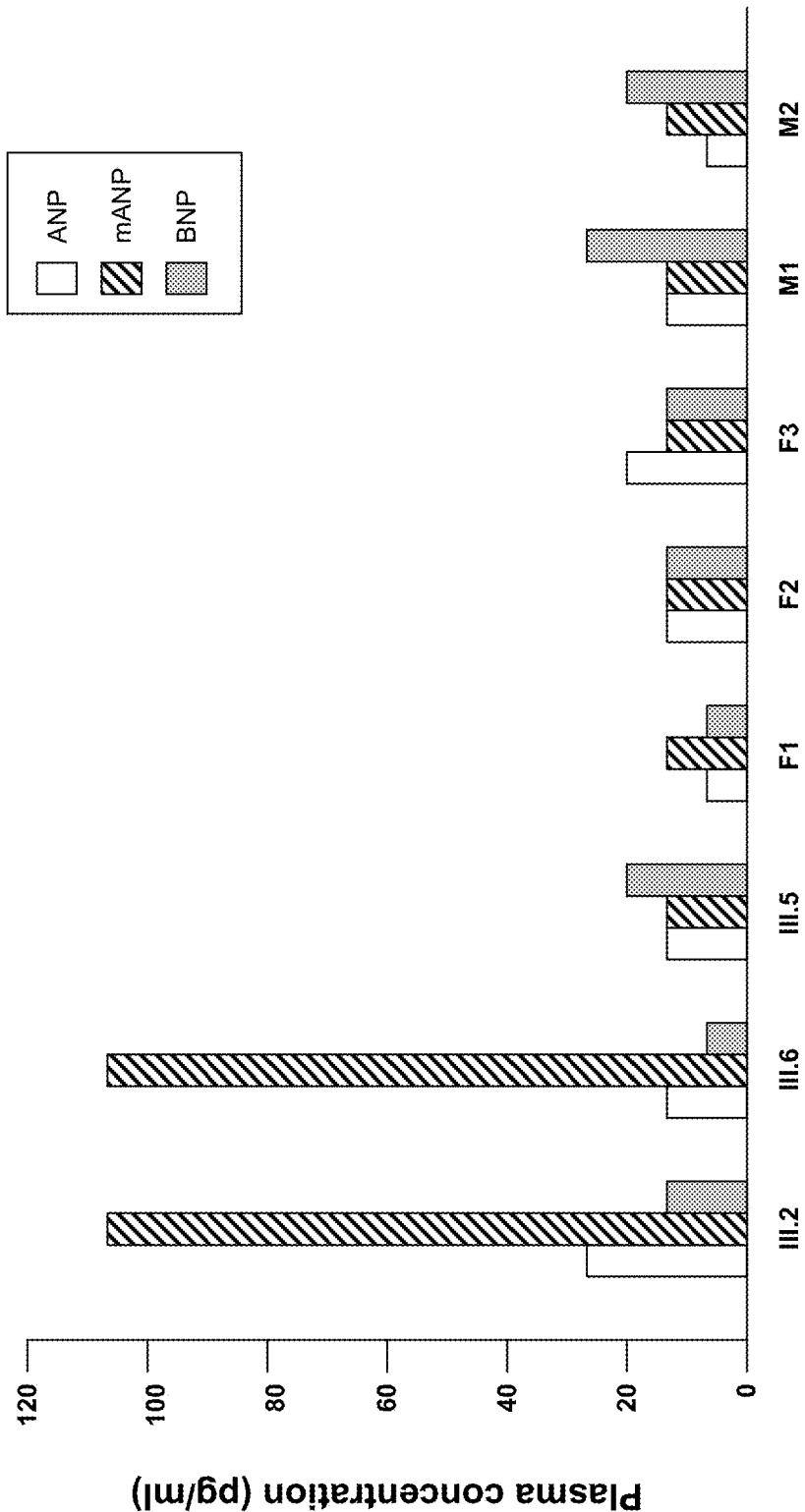
FIG. 3 is a graph plotting levels of mutant ANP protein in the plasma of family members affected with hereditary atrial fibrillation. A radioimmunoassay with polyclonal antibodies against wild-type atrial natriuretic peptide (ANP), mutant ANP (mANP), and brain natriuretic peptide (BNP) revealed normal plasma ANP and BNP levels together with circulating mANP at levels 5-10 fold that of ANP in family members with the NPPA-mutation (111.2 during chronic atrial fibrillation and 111.6 during normal sinus rhythm) compared to unaffected family members (III.5) and five normal controls. Low-level cross-reactivity of the polyclonal anti-mANP antibody was observed in unaffected and control samples. F, female; M, male.
Figure 4A:
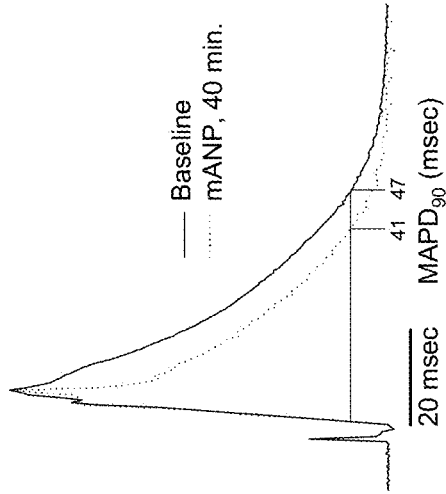
FIGS. 4A-4D are a series of graphs plotting atrial repolarization after treatment with mutant ANP or wild-type ANP.
Figure 4B:
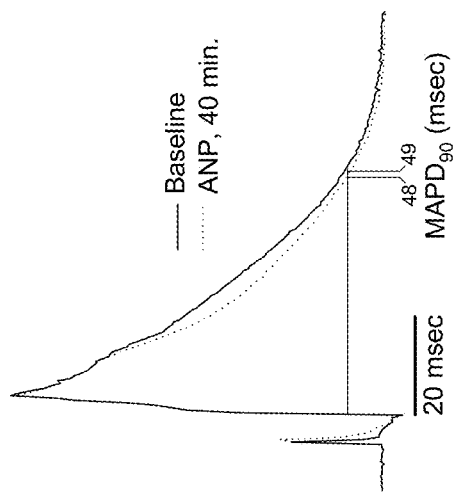
Figure 4D:
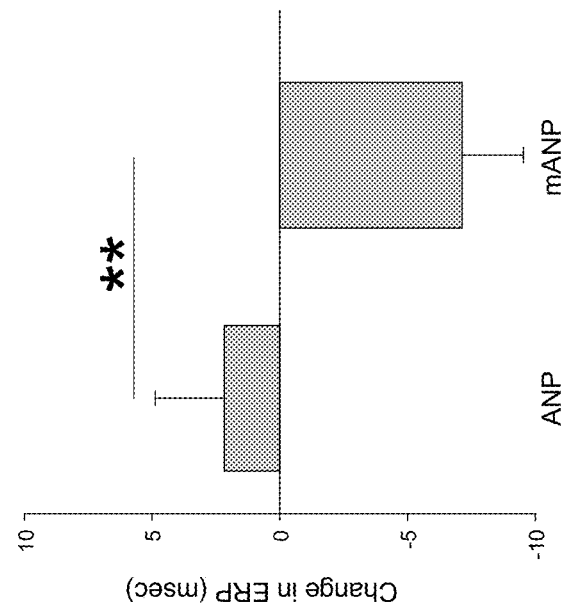
Figure 4C:
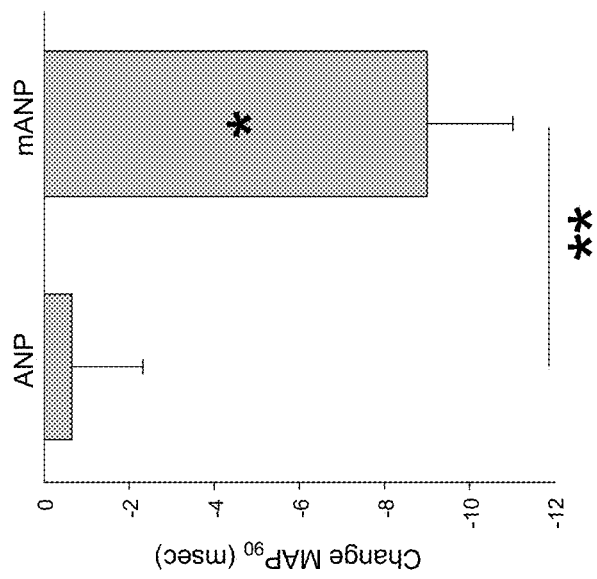

Radioimmunoassay demonstrated that the mutant peptide was present in the plasma of heterozygotes in concentrations 5- to 10-fold higher than wild-type ANP (FIG. 3). Anti-ANP was found to be specific for wild-type ANP, as the aberrant carboxyl-tail of mANP apparently prevented binding of this antibody. BNP levels were normal, consistent with lack of overt ventricular pathology (Levin et al., supra). To determine the integrative electrophysiological effects of circulating mANP on the heart, an isolated whole-heart model was studied. Compared to wild-type ANP, mANP caused significant shortening of the MAP duration and the ERP (FIGS. 4A-4D).

TABLE 2

Phenotypic data for family with autosomal dominant atrial fibrillation

| Pedigree number | Age Diag | Age Eval | Rhythm | HTN | Tachy CMO | LVH | LAE | LVDD | LVSD | % EF |
|---|---|---|---|---|---|---|---|---|---|---|
| II.2 | 58 | 69 | PAF > SB/JR | − | + | − | ++ | 54(48) | 36(32) | 60 |
| II.4 | 42 | 67 | PAF > SB/JR | + | − | − | − | 49(50) | 28(34) | 65 |
| II.5 | 51 | 66 | PAF > SB/JR | + | + | − | +++ | 66(53) | 40(36) | 50 |
| III.1 | 43 | 44 | PAF | + | − | − | − | nl | nl | 60 |
| III.2 | 45 | 41* | Chronic AF | + | + | − | − | 54(56) | 34(38) | 65 |
| III.3 | 38 | 43 | PAF | − | − | − | ++ | 50(54) | 35(36) | 60 |

TABLE 2-continued

Phenotypic data for family with autosomal dominant atrial fibrillation

| Pedigree number | Age Diag | Age Eval | Rhythm | HTN | Tachy CMO | LVH | LAE | LVDD | LVSD | % EF |
|---|---|---|---|---|---|---|---|---|---|---|
| III.4 | — | 35 | NSR | − | − | − | − | 58(56) | 35(40) | 65 |
| III.5 | — | 36 | NSR | − | − | − | − | 44(56) | 26(40) | 60 |
| III.6 | 30 | 45 | PAF | − | n/a | n/a | n/a | n/a | n/a | n/a |
| III.7 | — | 44 | "NSR" | − | − | n/a | n/a | n/a | n/a | n/a |
| III.8 | 37 | 38 | PAF > SB/JR** | − | + | − | + | 64(57) | 40(38) | 55 |
| III.9 | — | 38 | NSR | − | − | n/a | n/a | n/a | n/a | n/a |
| III.10 | 28 | 38 | Chronic AF | − | + | − | + | 56(57) | 39(38) | 50 |
| III.11 | — | 38 | NSR | − | − | − | − | 40(56) | 28(39) | 60 |
| III.12 | 35 | 36 | Chronic AF | − | − | − | +/++ | 54(53) | 38(36) | 55 |
| III.13 | 34 | 34 | PAF | − | − | − | + | 46(53) | 30(36) | 60 |

Echocardiographic measurements in affected individuals were made during effective ventricular rate control when AF was present.
*echocardiogram obtained prior to onset of atrial fibrillation.
**ventricular pacemaker implanted.
Diag, diagnosis;
Eval, evaluation;
−, not applicable or not present;
PAF, paroxysmal atrial fibrillation;
SB, sinus bradycardia;
JR, junctional escape rhythm;
NSR, documented normal sinus rhythm;
"NSR", NSR by history;
HTN, hypertension requiring treatment;
Tachy CMO, tachycardia-induced cardiomyopathy at initial diagnosis;
n/a, data unavailable;
LVH, left ventricular hypertrophy;
LAE, left atrial enlargement
(+, mild; ++, moderate; +++, severe); LVDD/LVSD, left ventricular diastolic/systolic dimension in mm (upper limits of normal for body surface area);
% EF, LV ejection fraction (normal ≥50).

Example 2 mANP Shortens Ventricular Refractory Period and Increases Ventricular Tachycardia Score Programmed electrical stimulation of the ventricles was performed across the diaphragm via bipolar electrode catheter placed through an abdominal incision in 10 week old male FVB mice anesthetized with inhaled isoflurane, and was continuously monitored by electrocardiogram. Electrophysiologic parameters were analyzed at baseline and after a 30 minute peritoneal infusion of saline vs. 33 pmol/kg/min ANP or mANP, following a 330 pmol/kg bolus. Summary data are presented in Table 3. The effective refractory period (ERP) was significantly shorter for the 30 minute mANP treatment group vs. the 30 minute saline group (ANOVA, $p<0.05$), while there was not a significant difference in ERP between the 30 minute ANP treatment group and the saline group. The ventricular tachycardia (VT) score was obtained by scoring 1 point for induction of sustained VT with a single extrastimulus, 2 points for induction with double extrastimuli, and 3 points for failure to induce with single or double extrastimuli. Nonsustained VT (less than 1 second) was not scored. The score for each of three mice in a group was added. A higher score indicates greater resistance to arrhythmia induction.

TABLE 3

Electrophysiologic parameters in anesthetized mice at baseline and in response to infusion of saline, ANP or mANP

| n = 3 each group | Heart rate (min$^{-1}$) | PR interval (msec) | QRST interval (msec) | ERP (msec) | VT score |
|---|---|---|---|---|---|
| Saline baseline | 345 + 33 | 47 + 7 | 16 + 1 | 34 + 1 | 3 |
| 30 min. saline | 245 + 10 | 73 + 6 | 24 + 2 | 34 + 1 | 4 |
| ANP baseline | 359 + 22 | 44 + 1 | 16 + 1 | 30 + 2 | 4 |
| 30 min. ANP | 255 + 8 | 73 + 4 | 23 + 1 | 28 + 2 | 3 |
| mANP baseline | 341 + 36 | 47 + 7 | 17 + 1 | 30 + 0 | 3 |
| 30 min. mANP | 243 + 16 | 76 + 4 | 26 + 1 | 19 + 4* | 5 |

Figure 6:
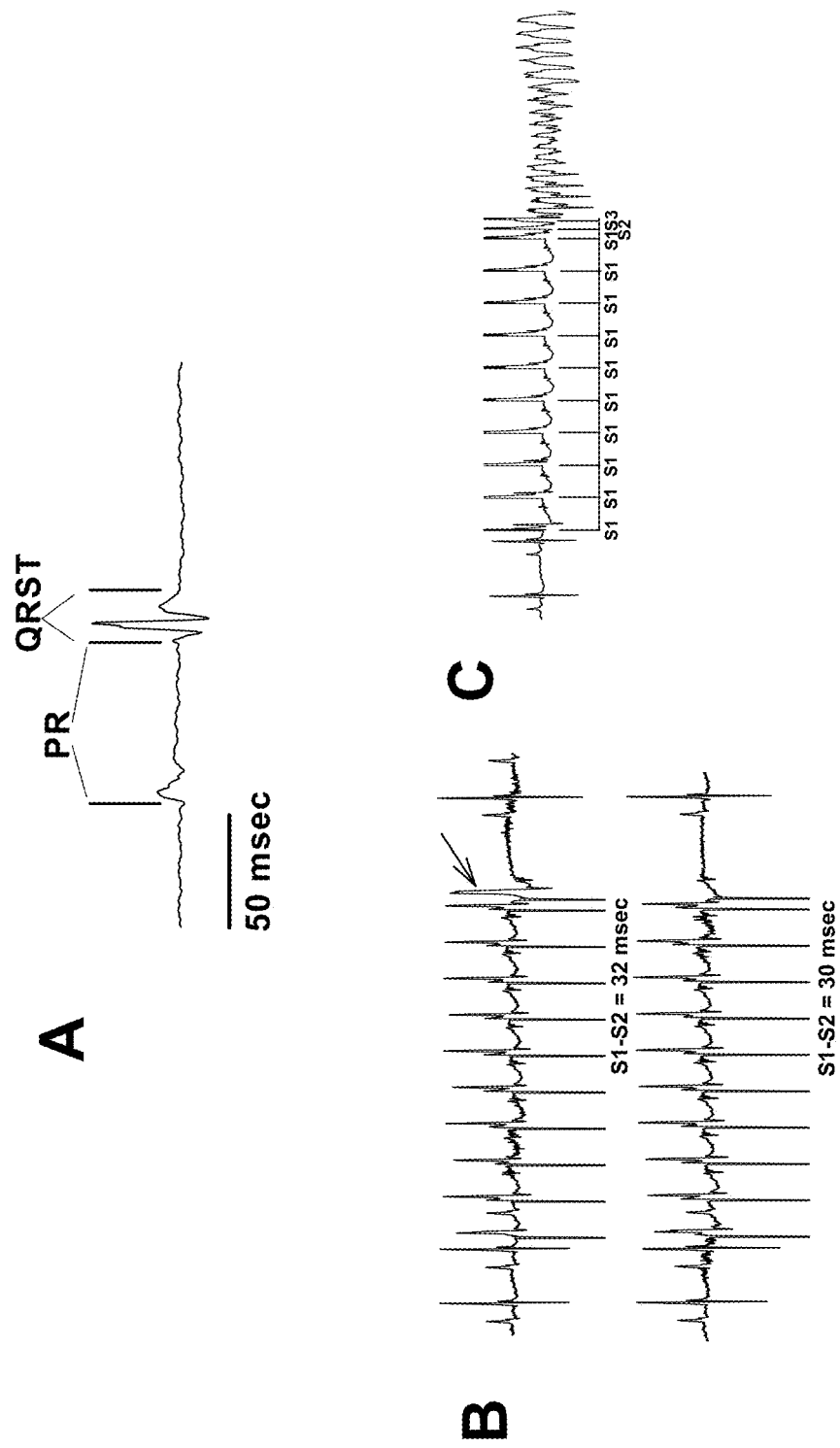
FIG. 6A is a graph plotting PR and QRST intervals derived from a non-paced electrocardiogram in sinus rhythm 30 minutes post ANP infusion.
FIG. 6B is a graph plotting effective refractory period (ERP) in a mouse at baseline. A train of 10 stimuli (S1) at 100 msec cycle length was followed by a single extrastimulus (S2) at progressively shorter coupling intervals. The top panel shows the S2 provoking a ventricular response, whereas the slightly shorter S2 coupling interval in the lower panel does not. The ERP shown is 30 msec.
FIG. 6C is a graph plotting induction of ventricular tachycardia (VT) in a mouse at baseline by a 10 beat pacing train at 100 msec cycle length (S1) followed by two extrastimuli (S2 and S3) each at 30 msec coupling interval.

PR and QRST intervals derived from a non-paced electrocardiogram in sinus rhythm 30 minutes post ANP infusion are shown in FIG. 6A, and the ERP at baseline is shown in FIG. 6B. A train of 10 stimuli (S1) at 100 msec cycle length was followed by a single extrastimulus (S2) at progressively shorter coupling intervals. The S2 in the top panel of FIG. 6B provoked a ventricular response, whereas the slightly shorter S2 coupling interval in the lower panel of FIG. 6B did not. The ERP shown is 30 msec. Induction of VT in a mouse at baseline by a 10 beat pacing train at 100 msec cycle length (S1) followed by two extrastimuli (S2 and S3) each at 30 msec coupling interval is shown in FIG. 6C.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a cardiac arrhythmia in a mammal in need thereof, comprising administering to the mammal an effective amount of a polypeptide comprising the amino acid sequence set forth in SEQ ID NO:6, with two amino acid additions, subtractions, or substitutions, wherein the polypeptide has a length between 17 and 45 amino acids and has natriuretic activity.

2. A method for treating a cardiac arrhythmia in a mammal in need thereof, comprising administering to the mammal an effective amount of a polypeptide comprising the amino acid sequence set forth in SEQ ID NO:6, with one amino acid addition, subtraction, or substitution, wherein the polypeptide has a length between 17 and 45 amino acids and has natriuretic activity.

3. A method for treating a cardiac arrhythmia in a mammal in need thereof, comprising administering to the mammal an effective amount of a polypeptide comprising the amino acid sequence set forth in SEQ ID NO:6, wherein the polypeptide has a length between 17 and 45 amino acids and has natriuretic activity.

* * * * *

SEQUENCE LISTING

<160> NUMBER OF SEQ ID NOS: 31

<210> SEQ ID NO 1
<211> LENGTH: 16
<212> TYPE: DNA
<213> ORGANISM: Homo sapiens

<400> SEQUENCE: 1
agtaccgaag ataaca                                                         16

<210> SEQ ID NO 2
<211> LENGTH: 16
<212> TYPE: DNA
<213> ORGANISM: Homo sapiens

<400> SEQUENCE: 2
agtactgaag ataaca                                                         16

<210> SEQ ID NO 3
<211> LENGTH: 13
<212> TYPE: PRT
<213> ORGANISM: Homo sapiens

<400> SEQUENCE: 3

Tyr Arg Ile Thr Ala Arg Glu Asp Lys Gln Gly Trp Ala
 1               5                  10

<210> SEQ ID NO 4
<211> LENGTH: 46
<212> TYPE: DNA
<213> ORGANISM: Homo sapiens

<400> SEQUENCE: 4
agtaccggat aacagccagg gaggacacgc agggctgggc ctaggg                        46

<210> SEQ ID NO 5
<211> LENGTH: 28
<212> TYPE: PRT
<213> ORGANISM: Homo sapiens

<400> SEQUENCE: 5

Ser Leu Arg Arg Ser Ser Cys Phe Gly Gly Arg Met Asp Arg Ile Gly
 1               5                  10                  15

Ala Gln Ser Gly Leu Gly Cys Asn Ser Phe Arg Tyr
            20                  25

<210> SEQ ID NO 6
<211> LENGTH: 40
<212> TYPE: PRT
<213> ORGANISM: Homo sapiens

<400> SEQUENCE: 6

Ser Leu Arg Arg Ser Ser Cys Phe Gly Gly Arg Met Asp Arg Ile Gly
 1               5                  10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 7
<211> LENGTH: 28
<212> TYPE: PRT
<213> ORGANISM: Oryctolagus cuniculus

```
<400> SEQUENCE: 7

Ser Leu Arg Arg Ser Ser Cys Phe Gly Gly Arg Ile Asp Arg Ile Gly
1               5                   10                  15

Ala Gln Ser Gly Leu Gly Cys Asn Ser Phe Arg Tyr
            20                  25

<210> SEQ ID NO 8
<211> LENGTH: 28
<212> TYPE: PRT
<213> ORGANISM: Danio rerio

<400> SEQUENCE: 8

Ser Lys Ser Leu Ser Gly Cys Phe Gly Gly Arg Leu Asp Arg Ile Gly
1               5                   10                  15

Ser Ser Ser Thr Leu Gly Cys Asn Ser Lys Lys Gly
            20                  25

<210> SEQ ID NO 9
<211> LENGTH: 32
<212> TYPE: PRT
<213> ORGANISM: Homo sapiens

<400> SEQUENCE: 9

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 10
<211> LENGTH: 22
<212> TYPE: PRT
<213> ORGANISM: Homo sapiens

<400> SEQUENCE: 10

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 11
<211> LENGTH: 38
<212> TYPE: PRT
<213> ORGANISM: Dendroaspis angusticeps

<400> SEQUENCE: 11

Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala
        35

<210> SEQ ID NO 12
<211> LENGTH: 32
<212> TYPE: PRT
<213> ORGANISM: Homo sapiens
```

```
<400> SEQUENCE: 12

Thr Ala Pro Arg Ser Leu Arg Arg Ser Ser Cys Phe Gly Gly Arg Met
 1               5                  10                  15

Asp Arg Ile Gly Ala Gln Ser Gly Leu Gly Cys Asn Ser Phe Arg Tyr
            20                  25                  30

<210> SEQ ID NO 13
<211> LENGTH: 12
<212> TYPE: PRT
<213> ORGANISM: Homo sapiens

<400> SEQUENCE: 13

Arg Ile Thr Ala Arg Glu Asp Lys Gln Gly Trp Ala
 1               5                  10

<210> SEQ ID NO 14
<211> LENGTH: 17
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 4
<223> OTHER INFORMATION: Xaa= Gly, Arg, Leu, or His
<220> FEATURE:
<221> NAME/KEY: VARIANT
<222> LOCATION: 5
<223> OTHER INFORMATION: Xaa= Arg or Lys
<220> FEATURE:
<221> NAME/KEY: VARIANT
<222> LOCATION: 6
<223> OTHER INFORMATION: Xaa= Met, Leu, or Ile
<220> FEATURE:
<221> NAME/KEY: VARIANT
<222> LOCATION: 10
<223> OTHER INFORMATION: Xaa= Gly, Ser, or Asn
<220> FEATURE:
<221> NAME/KEY: VARIANT
<222> LOCATION: 11
<223> OTHER INFORMATION: Xaa= Ala, Ser, or His
<220> FEATURE:
<221> NAME/KEY: VARIANT
<222> LOCATION: 12
<223> OTHER INFORMATION: Xaa=Gln, Ser, Met, or Val
<220> FEATURE:
<221> NAME/KEY: VARIANT
<222> LOCATION: 14
<223> OTHER INFORMATION: Xaa= Gly, Thr, or Asn

<400> SEQUENCE: 14

Cys Phe Gly Xaa Xaa Xaa Asp Arg Ile Xaa Xaa Xaa Ser Xaa Leu Gly
 1               5                  10                  15

Cys

<210> SEQ ID NO 15
<211> LENGTH: 40
<212> TYPE: PRT
<213> ORGANISM: Artificial Sequence
<220> FEATURE:
<223> OTHER INFORMATION: synthetic
```

<400> SEQUENCE: 15

Thr Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 16
<211> LENGTH: 40
<212> TYPE: PRT
<213> ORGANISM: Artificial Sequence
<220> FEATURE:
<223> OTHER INFORMATION: synthetic

<400> SEQUENCE: 16

Ser Ile Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 17
<211> LENGTH: 40
<212> TYPE: PRT
<213> ORGANISM: Artificial Sequence
<220> FEATURE:
<223> OTHER INFORMATION: synthetic

<400> SEQUENCE: 17

Ser Leu Lys Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 18
<211> LENGTH: 40
<212> TYPE: PRT
<213> ORGANISM: Artificial Sequence
<220> FEATURE:
<223> OTHER INFORMATION: synthetic

<400> SEQUENCE: 18

Ser Leu Arg Lys Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 19
<211> LENGTH: 40
<212> TYPE: PRT
<213> ORGANISM: Artificial Sequence
<220> FEATURE:
<223> OTHER INFORMATION: synthetic

<400> SEQUENCE: 19

Ser Leu Arg Arg Thr Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 20
<211> LENGTH: 40
<212> TYPE: PRT
<213> ORGANISM: Artificial Sequence
<220> FEATURE:
<223> OTHER INFORMATION: synthetic

<400> SEQUENCE: 20

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Arg Gln Gly Trp Ala
        35                  40

<210> SEQ ID NO 21
<211> LENGTH: 40
<212> TYPE: PRT
<213> ORGANISM: Artificial Sequence
<220> FEATURE:
<223> OTHER INFORMATION: synthetic

<400> SEQUENCE: 21

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Asn Gly Trp Ala
        35                  40

<210> SEQ ID NO 22
<211> LENGTH: 40
<212> TYPE: PRT
<213> ORGANISM: Artificial Sequence
<220> FEATURE:
<223> OTHER INFORMATION: synthetic

<400> SEQUENCE: 22

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Pro Trp Ala
        35                  40

<210> SEQ ID NO 23
<211> LENGTH: 40
<212> TYPE: PRT
<213> ORGANISM: Artificial Sequence
<220> FEATURE:
<223> OTHER INFORMATION: synthetic

<400> SEQUENCE: 23

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Tyr Ala
        35                  40

<210> SEQ ID NO 24
<211> LENGTH: 40
<212> TYPE: PRT
<213> ORGANISM: Artificial Sequence
<220> FEATURE:
<223> OTHER INFORMATION: synthetic

<400> SEQUENCE: 24

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Val
        35                  40

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ggagacaggg acagacgtag                                          20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
cccagactgc acccgctttc                                          20

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
gccaggaaag cgggtgcag                                           19

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
gggcactctg ggtgttggg                                           19

```
<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
gtgggaagca ggtggtcagt a                                              21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
agcttagatg ggatgatcac a                                              21

<210> SEQ ID NO 31
<211> LENGTH: 14
<212> TYPE: PRT
<213> ORGANISM: Homo sapiens

<400> SEQUENCE: 31

Cys Tyr Arg Ile Thr Ala Arg Glu Asp Lys Gln Gly Trp Ala
1               5                   10
```